(12) United States Patent
Tajima

(10) Patent No.: US 8,518,347 B2
(45) Date of Patent: *Aug. 27, 2013

(54) CARRIER ENCLOSING TIP, CARRIER TREATING APPARATUS AND METHOD OF CARRIER TREATMENT

(75) Inventor: Hideji Tajima, Matsudo (JP)

(73) Assignee: Universal Bio Research Co., Ltd., Matsudo-Shi, Chiba (JP)

( * ) Notice: Subject to any disclaimer, the term of this patent is extended or adjusted under 35 U.S.C. 154(b) by 825 days.

This patent is subject to a terminal disclaimer.

(21) Appl. No.: 11/794,828

(22) PCT Filed: Jan. 6, 2006

(86) PCT No.: PCT/JP2006/300064
§ 371 (c)(1),
(2), (4) Date: Dec. 10, 2009

(87) PCT Pub. No.: WO2006/073170
PCT Pub. Date: Jul. 13, 2006

(65) Prior Publication Data
US 2010/0119416 A1 May 13, 2010

(30) Foreign Application Priority Data

Jan. 7, 2005 (JP) ................. 2005-003251

(51) Int. Cl.
*B01L 3/02* (2006.01)
*B01D 21/00* (2006.01)
(52) U.S. Cl.
USPC ........... 422/509; 422/501; 422/511; 422/518; 422/521; 422/527; 422/528

(58) Field of Classification Search
USPC .......................... 422/501, 511, 521, 528, 509
See application file for complete search history.

(56) References Cited

U.S. PATENT DOCUMENTS 5,437,979 A * 8/1995 Rampal et al. ............... 435/6.16
6,660,233 B1 * 12/2003 Coassin et al. ................ 422/564
(Continued)

FOREIGN PATENT DOCUMENTS
JP 03-181853 8/1991
JP 05-281243 10/1993
(Continued)

OTHER PUBLICATIONS

Japanese Patent Office, "International Search Report," International Patent Application No. PCT/JP2006/300064, Apr. 4, 2006, 7 pages.

(Continued)

*Primary Examiner* — Brian R Gordon
(74) *Attorney, Agent, or Firm* — Haynes and Boone, LLP

(57) ABSTRACT

The invention relates to a carrier enclosing tip, a carrier treating apparatus, and a method of carrier treatment. An object is to perform separation/purification more efficiently and rapidly as compared with treatments using conventional liquid chromatography or filters. There is provided a carrier enclosing tip comprising: a tip-like container having a fitting opening which is fittable to a nozzle for use in gas suction and discharge, or a member to be fitted to a nozzle, and a port through which fluid inflow and outflow can be effected by the gas suction and discharge; and a carrier which is enclosed in the tip-like container, and is capable of adsorbing a biosubstance in the fluid or is capable of reacting with or binding to the biosubstance.

4 Claims, 14 Drawing Sheets

(56) References Cited

U.S. PATENT DOCUMENTS

| | | | | |
|---|---|---|---|---|
| 7,369,241 B2 * | 5/2008 | Tajima | ............................ | 356/432 |
| 2003/0064386 A1 * | 4/2003 | Karaki et al. | ........................ | 435/6 |
| 2005/0130325 A1 * | 6/2005 | Oshida et al. | ................... | 436/528 |

FOREIGN PATENT DOCUMENTS

| | | |
|---|---|---|
| JP | 05-506930 | 10/1993 |
| JP | 08-062225 | 3/1996 |
| JP | 09-262084 | 10/1997 |
| JP | 10-117764 | 5/1998 |
| JP | 10-323177 A | 12/1998 |
| JP | 2000-241436 | 9/2000 |
| JP | 2000-346842 | 12/2000 |
| JP | 2001-002695 | 1/2001 |
| JP | 2001-074756 | 3/2001 |
| JP | 2001-509256 A | 7/2001 |
| JP | 2002-102681 | 4/2002 |
| JP | 2002-513936 A | 5/2002 |
| JP | 2002-189033 | 7/2002 |
| JP | 2002-191351 A | 7/2002 |
| JP | 2003-107083 | 4/2003 |
| JP | 2003-531381 A | 10/2003 |
| JP | 2003-339374 A | 12/2003 |
| JP | 2004-033907 | 2/2004 |
| JP | 2004-061397 | 2/2004 |
| JP | 2004-294316 | 10/2004 |
| JP | 2004-359201 | 12/2004 |
| JP | 2004-359202 | 12/2004 |
| JP | 2005-030906 | 2/2005 |
| JP | 2005-278437 A | 10/2005 |
| JP | 2006-24502 | 9/2006 |
| JP | 2006-24503 | 9/2006 |
| JP | 2006-024504 | 9/2006 |
| JP | 2006-24505 | 9/2006 |
| JP | 2006-24527 | 9/2006 |
| WO | WO 00/67893 | 11/2000 |
| WO | WO 03/090729 A | 1/2003 |
| WO | WO 03/060115 | 7/2003 |
| WO | WO 2006/038643 | 4/2006 |
| WO | WO 2006/062235 | 6/2006 |
| WO | WO 2006/062236 | 6/2006 |

OTHER PUBLICATIONS

International Searching Authority "Written Opinion," Jan. 24, 2006, 4 pages, International Serial No. PCT/JP2005/018419, Japanese Patent Office.
International Searching Authority "International Search Report," Jan. 24, 2006, 2 pages, International Serial No. PCT/JP2005/018419, Japanese Patent Office.
International Searching Authority "International Search Report," Feb. 20, 2006, 4 pages, International Serial No. PCT/JP2005/022775, Japanese Patent Office.
International Searching Authority "Written Opinion," Feb. 28, 2006, 5 pages, International Serial No. PCT/JP2005/022775, Japanese Patent Office.
U.S. Appl. No. 11/664,980, filed Sep. 28, 2006, Hideji Tajima et al.
U.S. Appl. No. 29/277,775, filed Mar. 9, 2007, Hideji Tajima.
U.S. Appl. No. 29/277,777, filed Mar. 9, 2007, Hideji Tajima.
U.S. Appl. No. 29/277,778, filed Mar. 9, 2007, Hideji Tajima.
U.S. Appl. No. 29/277,779, filed Mar. 9, 2007, Hideji Tajima.
U.S. Appl. No. 29/277,780, filed Mar. 9, 2007, Hideji Tajima.
U.S. Appl. No. 11/792,783, filed Jun. 8, 2007, Hideji Tajima.
U.S. Appl. No. 11/792,835, filed Jun. 8, 2007, Hideji Tajima.
International Searching Authority "Written Opinion," Mar. 7, 2006, 5 pages, International Serial No. PCT/JP2005/022776, Japanese Patent Office.
International Searching Authority "International Search Report," Mar. 7, 2006, 4 pages International Serial No. PCT/JP2005/022776, Japanese Patent Office.
International Preliminary Examination Authority, "International Preliminary Examination Report on Patentability," Oct. 3, 2006, 13 pages, International Serial No. PCT/JP2005/018419, Japanese Patent Office.
International Preliminary Examination Authority, "International Preliminary Examination Report on Patentability," Nov. 29 2006, 8 pages, International Serial No. PCT/JP2005/022776, Japanese Patent Office.
International Preliminiary Examination Authority,"International Preliminary Examination Report on Patentability," Dec. 12, 2006, 11 pages, International Serial No. PCT/JP2005/022775, Japanese Patent Office.

* cited by examiner

CARRIER ENCLOSING TIP, CARRIER TREATING APPARATUS AND METHOD OF CARRIER TREATMENT

CROSS REFERENCE

This application is a United States national phase application of co-pending international patent application number PCT/JP2006/300064, filed Jan. 6, 2006, which claims priority to Japanese patent application number 2005-003251, filed Jan. 7, 2005, the disclosures of which are incorporated herein by reference.

TECHNICAL FIELD

The present invention relates to a carrier enclosing tip, a carrier treating apparatus, and a method of carrier treatment.

BACKGROUND ART

Conventionally, there has been liquid chromatography using a principal of liquid chromatography in which a cylindrical container, called a column, having a liquid inlet and outlet in the center of an upper and lower circular plates, is filled with a particulate filler, called a gel, having a particle diameter of ten to several hundred microns, so that separation/purification of a substance is performed utilizing the interaction between solute molecules and conclusion when a liquid is made to flow from either the upper or lower liquid inlet or outlet by a pump or the like. Currently, various gels for liquid chromatography having different surface structures are commercially available. Gels whose surface displays ion exchange groups, function as an ion exchange gel, which is capable of separation of a substance by means of ion exchange chromatography utilizing the interaction of ionic charges with solute molecules.

Incidentally, these chromatography separation systems have been applied as a system of a complicated structure combined with; a pump for making liquids flow through the column, a container for containing these liquids, a valve for appropriately switching the passage, and measuring equipment for detecting the absorbance, pH, the electrical conductivity of an object substance flowing out from the column.

Normally, separation of a substance in chromatography involves a method for combining columns at several steps to achieve a required purified purity. Two or three steps of chromatography are often combined such as ion exchange chromatography→hydrophobic chromatography→gel filtration chromatography. However, in reality, when a substance is searched for and examined for use in research and development, only one or two steps of chromatography are sufficient in many cases. However, even when only one step of chromatography is performed, there is a problem in that the liquid chromatography system is likely to be a large scale system combined with a pump, a passage switching system, a column, containers for chromatography developing solutions, a detection system, and the like.

Moreover, even in such a large scale system, each specimen can be treated only one by one. Therefore in conventional liquid chromatography there is also a problem in that the treatment efficiency is low. Moreover there is a problem in that the flow direction is limited to one way only.

[Non Patent Document 1] "Liquid Chromatography Q&A" (published by Gihodo Shuppan Co., Ltd., June 2006, written by Itaru Matsushita)

[Non Patent Document 2] "Reality of Liquid Chromatography" (published by Sankyo Publishing Co. Ltd., 1976, written by Akira Etoh)

DISCLOSURE OF THE INVENTION

Problems to be Solved by the Invention

Here, a first object of the present invention is to provide a carrier enclosing tip, a carrier treating apparatus, and a method of carrier treatment capable of increasing the separation performance of conventional liquid chromatography or filters.

A second object is to provide a carrier enclosing tip, a carrier treating apparatus, and a method of carrier treatment capable of performing separation/purification more efficiently and rapidly as compared with treatments using conventional liquid chromatography or filters.

A third object is to provide a carrier enclosing tip, a carrier treating apparatus, and a method of carrier treatment capable of realizing the separation performance with a simpler structure as compared with the structure for treatments using conventional liquid chromatography or filters.

A fourth object is to provide a carrier enclosing tip, a carrier treating apparatus, and a method of carrier treatment which facilitate the automization of consistent treatment using liquid chromatography or filters.

Means for Solving the Problems

A first aspect of the present invention is a carrier enclosing tip comprising: a tip-like container having a fitting opening which is fittable to a nozzle for use in gas suction and discharge, or a member to be fitted to a nozzle, and a port through which fluid inflow and outflow can be effected by the gas suction and discharge; and a carrier which is enclosed in the tip-like container, and is capable of adsorbing or capturing a biosubstance in the fluid or is capable of reacting with or binding to the biosubstance.

Here, the term "carrier" refers to an insoluble solid matter capable of adsorbing, reacting with, binding to, fixing, or capturing a biosubstance in fluid, which may be in any shape such as particulate, block-shape, thin membranous, thin plate-shape, membranous, plate-shape, or indeterminate form. There is no restriction on the number of solid matters, and the carrier does not necessarily comprise one solid matter, but may comprise a plurality of solid matters. Furthermore, the size of the carrier varies and may be or may not be capable of passing through the port. Examples of the material of the carrier include a gel, a porous body, a permeable porous body, and a water bearable matter, formed from resins or fibrous matters such as a rubber, a silicone, a cellulose, and a nylon, and metals such as nonmagnetic particles, and magnetic particles. The carrier is provided with a chemical substance such as a functional group or a biosubstance, for adsorbing, reacting with, binding to, fixing, or capturing a biosubstance. Examples of the substance provided on the surface of the carrier include affinity ligands and affinity tags such as an antigen, an antibody, an enzyme, a substrate, a receptor, and a His-tag. A filler and a filter are examples of such a carrier. Examples of a thin membranous carrier include an ultrafiltration membrane for performing ultrafiltration of a protein.

The term "filler" refers to an insoluble stationary phase which is, based on the principal of liquid chromatography, selected for absorbing an object biosubstance contained in a predetermined fluid serving as a so-called mobile phase, and is to be filled into a predetermined container. Here, the filler is for example, those having a predetermined carrier whose surface is provided with or bonded to the above-mentioned substance.

The term "biosubstance" includes biopolymers or low molecular materials, for example, genetic materials such as a nucleic acid, proteins, sugars, sugar chains, peptides, and pigments. Examples of the biosubstance include a cell, a virus, and a plasmid. The biosubstance can be also used as a detection material which detects the bonding of a receptor biosubstance that is bindable to the biosubstance, as a ligand, and captures, separates, and extracts the receptor biosubstance. As to the receptor, biosubstances including genetic materials such as a nucleic acid, proteins, sugar chains, and peptides which are bindable to respective abovementioned genetic materials such as a nucleic acid, proteins, sugar chains, and peptides, are appropriate. Moreover, the term "filter" refers to a member for use in separation of a substance by absorbing or setting a predetermined pore diameter.

Here, the term "permeable porous block" refer to a structure in which a three-dimensional network skeleton and its voids (also referred to as passages, micropores, and through pores) are integrated. The skeleton size and the passage size can be independently determined. Increase in the passage size enables suction and discharge at a lower pressure as compared with that of a particulate filler. However, as the percentage of voids is increased, the absorption capacity and the surface area are decreased (BIO INDUSTRY, Vol. 21, No. 11, 2004).

The term "adsorbing or capturing the biosubstance or reacting with, or binding to the biosubstance" refers to, for example, cases of covalent bonding, chemical absorption, physical adsorption, capturing by means of electrical interaction or a predetermined pore diameter, specific reaction with a predetermined chemical substance provided on the carrier by means of chemical or physical adsorption or with a binding substance fixed to the carrier, and reacting or binding by other methods. Moreover, the reacting ability and the binding ability with respect to various substances including biosubstances may be improved by forming the carrier from a porous member, a rugged member, or a fibrous member. In order to fix a complementary biosubstance to the carrier so as to react with or bind to a biosubstance, the carrier is designed so that a functional group can be expressed or generated. To achieve this, the functional group for use in fixing of the biosubstance can be expressed or generated by, for example, hydrolyzing a peptide linkage of silk comprising "polyamide based polymer", nylon (such as 3-nylon, 6-nylon, 6,6-nylon, 6,10-nylon, 7-nylon, and 12-nylon), all aromatic polyamide such as PPTA (polyparaphenylen terephthalamide), heterocycle-containing aromatic polymer, or the like. Examples of the functional group bindable to the biosubstance include a carboxyl group —COOH, an amino group —$NH_2$, and derivatives thereof. Here, the pore diameter suitable for fixing the biosubstance is, for example, several micrometers or less.

Examples of the "member to be fitted to a nozzle" include a tip and an adaptor. The "tip" comprises a large diameter tube and a small diameter tube which is communicated with the large diameter tube, and is formed to be narrower than the large diameter tube. The large diameter tube has a fitting opening which is fitted or fittable to a nozzle, and the small diameter tube has a port through which fluid inflow and outflow can be effected by gas suction and discharge.

The term "tip-like container" refers to a container which has a port and a fitting opening which is fitted or fittable to a member for use in suction and discharge, and is capable of accommodating a carrier. The tip-like container preferably has a wide tube and a narrow tube, whose shape is not limited to a typical tip-form having a large diameter tube and a small diameter tube. In this case, preferably, at the tip of the narrow tube is provided a port and on the upper side of the wide tube is provided a fitting opening. For example, the wide tube may be in a quadratic prism-shape instead of a large diameter tube, and the narrow tube may be a prism-shaped tube instead of a small diameter tube. Furthermore, the carrier is accommodated in, for example, a part corresponding to the wide tube, or a part corresponding to a transition portion between the wide tube and the narrow tube. The volume of the tip-like container is preferably capable of handling a fluid of several microliters to several hundred microliters. Moreover, the tip-like container may be provided with a storage tube which stores a fluid introduced from the port, together with a part where the carrier is enclosed and accommodated. The storage tube is preferably formed wider than the narrow tube and the wide tube. The narrow tube may be provided either integrally with the wide tube or the storage tube, or detachably therefrom. Moreover, the wide tube itself may be provided either integrally with the storage tube, or detachably therefrom.

The material of the tip-like container is preferably transparent so as to enable optical observation. Examples of the material of the tip-like container include resins such as polyethylene, polypropylene, polystyrene, and acrylic resin, a glass, metals, and metal compounds. The size is, for example, capable of accommodating a liquid of several microliters to several hundreds microliters in the narrow tube.

A second aspect of the present invention is a carrier enclosing tip, wherein the tip-like container comprises: a carrier accommodating tube which accommodates the carrier; and a flow tube which is communicated with the carrier accommodating tube, is provided on a lower side of the carrier accommodating tube, and is formed narrower than the carrier accommodating tube; and the fitting opening is provided on an upper side of the carrier accommodating tube, and the port is provided at a tip of the flow tube.

The upper side of the carrier accommodating tube may be provided with a storage tube which is communicated with the carrier accommodating tube, and is capable of storing a fluid flowing from the port, and the fitting opening may be provided on the upper side of the storage tube. By so doing, a fluid can be introduced into the upper side from the carrier accommodating tube, and thus a larger amount of fluid than the capacity of the passage and the carrier accommodating tube can be brought into contact with the carrier. In this case, the storage tube is preferably formed wider than the carrier accommodating tube. By so doing, a step or slope between the carrier accommodating tube and the storage tube and/or a step or slope between the carrier accommodating tube and the passage can be utilized to latch and reliably hold the carrier passage prevention member or the carrier.

A third aspect of the present invention is a carrier enclosing tip, wherein the tip-like container is provided with an enclosing section which encloses the carrier in the tip-like container so that the carrier can be in contact with a fluid that has flown into the tip-like container.

Examples of the "enclosing section" include: a permeable porous member, a permeable member such as a mesh-like member through which the carrier can not pass but a fluid can pass, or the like that is provided separately from the tip-like container; the tip-like container itself, such as the tip-like container whose wall is deformed or processed to provide the enclosing section; or a combination of a separate member and the tip-like container whose wall or the like is processed. In addition, the enclosing section may be provided separately from the tip-like container, as a movable one, which can not pass through the port whereas the filler itself can pass through the port, and is connected to the carrier. Examples of the enclosing section using the tip-like container itself include those provided with a projection or the like projecting toward the center of the tube so as to narrow the tip-like container in a contracting manner. Furthermore, another example of the enclosing section is a spacer member which is provided either separately from the tip-like container or by processing the tip-like container, for enclosing the carrier in a manner to avoid adhesion with the tip-like container to facilitate a fluid to pass smoothly through the carrier. The term "enclose" refers to a state where the carrier is not discharged from the port and the fitting opening by the flow of a fluid, including cases where the carrier is attached to the tip-like container, and cases where the carrier is locked up within a part of the region in the tip-like container.

Of these enclosing sections, the "permeable porous member" does not necessarily have to be a filter which captures a certain substance by absorption or the like. However, if the material of the enclosing section is a filter or a thin membranous filter such as a membrane, the enclosing section is not only capable of preventing the outflow of the carrier from the port and the fitting opening, but also is capable of capturing a predetermined substance. If the enclosing section is provided separately from the tip-like container, a member formed in thin plate-shape or thin membranous-shape that is thin in the flow direction of a fluid is used, or a permeable member having a large pore diameter is used with a condition that the filler does not flow out. Moreover, if an enclosing section is provided by processing the tip-like container, the pressure required for suction and discharge can be reduced by enlarging the opening with a condition that the filler does not flow out.

A fourth aspect of the present invention is a carrier enclosing tip, wherein the enclosing section has one or more carrier passage prevention members provided separately from the tip-like container so as to partition between the port and the fitting opening of the tip-like container, so that the carrier can be in contact with a fluid that has flown thereinto.

Here, the "carrier passage prevention member" is formed from a separate member from the tip-like container. The wall of the tip-like container, a combination of a separate member and a processed wall of the tip-like container, or the like may be also used. The carrier passage prevention member is capable of letting a fluid pass through by, for example, having a through hole or being formed with a clearance between the member and the inner wall surface of the tip-like container, where the size or the shape of the through hole or the clearance does not allow the carrier to pass through. Examples thereof include members in a wheel form, a cross form, an I-form, a radial form, a mesh form, or a ring form provided to partition the narrow tube, and a permeable porous member.

Examples of the enclosing section using the tip-like container itself include those provided with a projection projecting toward the center of the tube so as to narrow the tip-like container in a contracting manner. Moreover, the enclosing section may be connected with the carrier.

In order to prevent the outflow of the carrier from both of the port and the fitting opening, the number of the carrier passage prevention members is preferably at least two so as to sandwich the carrier from both sides of the port and the fitting opening.

Here, use of the permeable porous member enables common and reliable enclosure of various carriers having a greater size than the pore diameter.

By detachably providing the separate carrier passage prevention member, the carrier can be readily enclosed and taken out.

If the abovementioned storage tube is formed wider than the carrier accommodating tube, the carrier passage prevention member can be latched and held using a slope or step between the storage tube and the carrier accommodating tube, to thereby prevent the carrier from entering the storage tube and reliably provide the carrier passage prevention member.

A fifth aspect of the present invention is a carrier enclosing tip, wherein the enclosing section is provided with: a projection which projects inward so as to partition an inner wall surface of the tip-like container between the fitting opening and the port, on the inner wall surface; and a slope which is tapered toward the port, or a step which is provided projecting inward and facing away from the port.

As a result, the enclosing section is provided by processing or deforming the tip-like container, and thus the carrier can be reliably attached to or enclosed in the tip-like container. Here, the "projection" and the "step" may be formed so as to project or be provided projectingly at a same height inward from the inner wall, or in a same thickness facing away from the port, as well as being formed at different heights or in different thicknesses. If the "projection" or the "step" projects or is provided projecting inward at a uniform and high height, preferably, the "projection" or the "step" supports the carrier as an enclosing section, by having the spacer member therebetween. As a result, a fluid can smoothly pass through the whole carrier.

A sixth aspect of the present invention is a carrier enclosing tip, wherein the carrier is a filler comprising a plurality of particulate carriers. Here, the size of the particulate carrier is capable of passing through the port, and is capable of being enclosed in the tip-like container by the enclosing section.

A seventh aspect of the present invention is a carrier enclosing tip, wherein the carrier is a permeable porous block-shaped filler or a block-shaped filter. Here, the term "block-shape" includes a column-shape, a prism-shape, and a globular-shape.

An eighth aspect of the present invention is a carrier enclosing tip, wherein the projection, slope, or step latches the carrier or the carrier passage prevention member to the tip-like container, and holds therein.

A ninth aspect of the present invention is a carrier enclosing tip, wherein all, or a part, of a wall of the tip-like container is formed from a conductive member having a predetermined electrical resistance.

Here, by providing a conductive member in the tip-like container, heat can be generated in such a manner that the conductive member having a predetermined resistance is brought into contact with a terminal which is connected to a power circuit provided outside of the conductive member, and is supplied with an electrical current. The current value is controlled by a controller described later, in accordance with the treatment contents.

Here, the "predetermined electrical resistance" is a value at which the conductive member can perform heat generation necessary to achieve a temperature according to the purpose, by supplying a predetermined current to the conductive member. For example, the surface resistance value ranges from about several hundreds ohms to several ohms per unit area, and the resistance value capable of induction heating is several ohms cm or more. For example, the conductive thin membrane comprises single type of material having a predetermined electrical resistance in some cases, and comprises two or more types of materials having different resistance values which are joined, deposited, vacuum-evaporated, fused, welded, bonded, adhered, or pasted together, in other cases. In the former case, the temperature depends on the magnitude of the current value as an electromagnetic signal.

In the latter case, the temperature depends not only on the current value, but also on the direction of the current due to the Peltier effect, and thus cooling is possible as well as heating.

Examples of the "conductive member" include metals, metal compounds such as metal oxides, conductive materials such as alloys, semiconductors, metalloids, and conductive resins, combinations of these conductive materials with non conductive materials such as ceramics, glass, and a synthetic resin, and combinations between conductive materials. For example, two members formed from different types of conductive materials such as aluminum, aluminum oxide, tin oxide, iron, iron alloy, and nichrome alloy are connected by adhesion, welding, or joining, in some cases. Induction heating can be performed on these members by supplying a current to the members, or, in cases of iron or iron alloy, by applying a magnetic filed which fluctuates with time. In cases where two types of conductive materials are joined, heating and cooling can be performed by orientation of the current.

Examples of the shape of the conductive member include a linear form, a thin membranous form, a foil-like form, a membranous form, a thin plate-form, a plate-form, a slender form, and a laminar-form. The conductive member may be adhered, deposited, or vacuum-evaporated on a nonconductive member so as to reinforce the conductive member. The conductive member is controlled to a predetermined temperature by an "electromagnetic signal" (electrical signal or magnetic signal). The electromagnetic signal does not include thermodynamic signals resulting from the application of heat or cold air.

The tip-like container has a wall in which the inner wall surface faces the inside of the tip-like container, the outer wall surface is outside of the tip-like container, and the interval between the inner and outer wall surfaces is integrally formed. That is, the wall portion sandwiched between the inner wall surface and the outer wall surface of the tip-like container is formed as an undividable wall from, for example; a metal, a resin, and a combination having them bonded in a solid state. Therefore, the conductive member formed either as the entire or a part of the wall, does not include, cases where the conductive member is detachable from the wall, for example, conductive members which are merely in contact with the wall, conductive members which are removably attached to the wall with screws or the like, conductive members which are removably attached to a separate member attached to the wall by welding or the like, and conductive members which are completely separated from the wall, since they are dividable. Accordingly, if the conductive member is provided so that the wall of the tip-like container approximately satisfies the requirement in the thickness as the wall of the tip-like container, the size of the tip-like container and the scale of the whole apparatus can be controlled, and handling can be performed without a consideration of the existence of a heating device.

A tenth aspect of the present invention is a carrier enclosing tip, wherein a volume of a space capable of accommodating a fluid in the tip-like container enclosing the carrier is about several microliters to several hundred microliters.

Here, the term "space capable of accommodating a fluid" roughly refers to a space made between the inner wall of a portion of the tip-like container where a fluid is accommodated, and the surface of the enclosed carrier.

By limiting the volume in such a manner, even if a minute amount of liquid, that is, a liquid having a volume of several microliters to several hundred microliters, is sucked into the tip-like container, the liquid can be brought into a uniform and even contact with the surface of the carrier. This kind of minute amount is often handled as a substance readily extracted from a living body, normally in biochemistry, particularly in the field of DNA.

An eleventh aspect of the present invention is a carrier enclosing tip, wherein the tip-like container comprises: a wide tube; a narrow tube which is formed narrower than the wide tube; and a transition portion between the wide tube and the narrow tube; and the fitting opening is formed in the wide tube, the port is formed at a tip of the narrow tube, and the enclosing section utilizes a step or slope of the transition portion so as to provide the carrier or carrier passage prevention member in the tip-like container.

Here, the wide tube or the transition portion correspond to the carrier accommodating tube, and the narrow tube corresponds to the passage. Furthermore, a widest tube which is wider than the wide tube may be provided as a storage tube, so that a step or slope between the wide tube and the widest tube is utilized to latch and hold the carrier passage prevention member therein.

A twelfth aspect of the present invention is a carrier enclosing tip, wherein, as the enclosing section, there are provided: a projection which projects inward so as to partition an inner wall surface of the tip-like container between the fitting opening and the port, on the inner wall surface; and a slope which is tapered toward the port, or a step which is provided projecting inward facing away from the port, at least in two points while being separated from each other, along a direction linking the fitting opening and the port, and at least one of these projection, slope, and step is used to enclose the carrier in the tip-like container.

Here, examples of the carrier include membranous and thin plate-shaped filters, particulate filters, and block-shaped filters. For example, if the carrier is a membranous or thin plate-shaped filter, usage of the projection or the like and an additional enclosing section provided as a separate body enables a further reliable enclosure or a reliable contact with a fluid. For example, the reliable enclosure and the reliable contact are performed: by mounting the membranous filter (under which an auxiliary mesh member may be placed as required) on a spacer member, as a first other enclosing section, that has been provided on a step or the like of the tip-like container for use in the enclosure of the filter, and is formed in a thin plate-shape as a whole, which has, for example, a rim provided to surround the center of the tip-like container so as to be in contact with the inner wall surface of the tip-like container, and a member projecting toward the center from the rim; and by using a cylindrical sleeve, as a second enclosing section, whose side face is in contact with the inner wall of the tip-like container and is attached to engage so as to surround the axis of the tip-like container, on top of the membranous filter; so that the thin membranous filter is sandwiched from the top and the bottom, and attached on the upper side of the projection or the like. Examples of the membranous filter and the thin plate-shaped filter include ultrafiltration membranes which can absorb proteins. Moreover, for example, in order to enclose a large number of particulate carriers utilizing the projection or the like, two of the projections or the like which are separated from each other are used and attached with an enclosing section or a filter (such as a microfiltration membrane) which respectively blocks the particulate carriers, and the particulate carriers are enclosed and held between these two projections or the like. The reliable enclosure of the carrier enables contact between a fluid and the carrier not only by fluid discharge but also by fluid suction.

A thirteenth aspect of the present invention is a liquid chromatography separation apparatus comprising: a nozzle head having either one or a plurality of nozzles which perform gas suction and discharge; a suction and discharge mechanism which performs gas suction and discharge through the nozzle; one or more carrier enclosing tips which are fitted or fittable to the nozzle or a member to be fitted to the nozzle, and enclose a carrier capable of adsorbing or capturing a biosubstance in a fluid, or capable of reacting with or binding to the biosubstance; a stage provided with a group of liquid accommodating sections which accommodate or are capable of accommodating various liquids; a moving device which moves the nozzle head relatively to the group of liquid accommodating sections; and a controller which controls an amount, a speed, a number of times, a time, or a position of suction and discharge performed by the nozzle, according to material conditions including a structure of the nozzle, a member to be fitted to the nozzle, and the carrier enclosing tip, the type and concentration of a biosubstance in the fluid, the amount of the fluid, the temperature of the fluid or the carrier, and the coordinate position including the position of accommodation of the fluid, and the treatment contents.

Here, the term "treatment contents" refers to, for example, reaction, washing, transfer, dispensation, separation, extraction, heating, cooling, clarification, measurement, mixing, dissociation, elution, agitation, or a series of these treatments combined, including repetition, in accordance with a predetermined sequence or a predetermined time schedule according to the purpose of treatment. The term "time" includes a duration and a timing of suction and discharge. Setting of the duration or timing enables setting of intermittent, continuous, or noncontinuous suction and discharge.

In cases of "reaction" treatment, for example, according to the material conditions, the suction and discharge determined by the conditions, are controlled to repeat at a predetermined speed with a liquid volume of, for example, 80% of the capacity of the carrier enclosure region in the narrow tube, in a position of a container accommodating a corresponding reagent. The number of times of the suction and discharge is also controlled based on the determination according to the material conditions. In cases of "washing" treatment, for example, according to the material conditions, the suction and discharge are controlled to repeat for a predetermined time at a predetermined speed determined in accordance with the treatment, in a position of a container accommodating a washing solution. The suction and discharge are controlled according to the treatment in the same manner. Regarding the "speed", for example, when a substance to be handled is DNA, the size is smaller than that of a protein, and thus the speed needs to be increased in order to increase the chance of encounter between DNA. Moreover, the speed differs depending on the treatment contents, and the speed of suction and discharge for washing or agitation is lower than the speed for reaction treatment. Furthermore, for example, with respect to a carrier of an absorption type separation membrane, suction is appropriately performed at a linear flow rate (a value obtained by diving the volume flow rate by the sectional area) of about 10 to 50 cm per hour. If the carrier is an ultrafiltration membrane, since the flow is one-way, a control which makes a fluid pass by means of suction or pressurization, is required. On the other hand, if the carrier is a filler, suction of a sample solution with a tip enables the filler to float so that a suitable condition of contact between a separating agent and an object substance contained in the sample can be achieved. Moreover, in cases of separation in conventional chromatography, the volume of absorption, so-called dynamic capacity is inversely proportional to the flow rate, and the rate of adsorption decreases. However, control of the speed of suction and discharge can realize a volume of adsorption closer to batch absorption.

The term "structure of tip" includes the shape of the tip, and the term "structure of carrier enclosing tip" includes the shape of the tip-like container, the position of a carrier enclosed therein, the shape, the type, and the property of the accommodated carrier, and the shape of the enclosing section. The determination of the operation of suction and discharge according to the "type of the biosubstance" means, for example, to achieve easier handling with less amount of liquid to be handled at a higher speed in cases of biosubstances such as DNA whose size is typically smaller than that of a protein. The reason is that, as the size is smaller, the chance of encounter typically decreases.

A fourteenth aspect of the present invention is a carrier treating apparatus, wherein a volume of a space capable of accommodating a fluid in a tip-like container enclosing the carrier is about several microliters to several hundred microliters.

Accordingly, the liquid accommodating section provided outside of the carrier enclosing tip must be able to accommodate the liquid of about several microliters to several hundred microliters in a manner such that the liquid can be sucked into the narrow tube through the port of the narrow tube.

A fifteenth aspect of the present invention is a carrier treating apparatus, wherein a temperature increasing/decreasing member which increases/decreases the temperature by external signals, is provided close to, or so as to be capable of coming close to, the outside of the tip-like container of the carrier enclosing tip.

Here, the term "temperature increasing/decreasing member" refers to a member which is capable of increasing/decreasing the temperature according to external signals. The term "signal" refers to an electromagnetic signal, that is, an electrical signal or magnetic signal, if the temperature increasing/decreasing member is a conductive member. The increasing/decreasing member may be also designed to be capable of detecting the temperature to generate a signal based on the temperature.

Preferably, the temperature increasing/decreasing member is provided in a relatively movable manner with respect to the carrier enclosing tip. Moreover, in this case, the controller controls the temperature as well as the suction and discharge, based on the treatment contents.

A sixteenth aspect of the present invention is a carrier treating apparatus, wherein: the nozzle head has a single individual nozzle and a plurality of consecutive collective nozzles arranged in the row direction, both of which are arranged in the row direction; the suction and discharge mechanism performs gas suction and discharge with respect to the single individual nozzle and the plurality of collective nozzles of the nozzle head at once; and the moving device comprises a nozzle head moving device which moves the nozzle head relatively to the group of accommodating sections along the line direction, and a line and row path conveyance device which has a conveyance path including a row conveyance path on the movement path of the collective nozzles along the row direction and a line conveyance path on the movement path of the individual nozzle along the line direction, and conveys tip-like containers detached from the collective nozzles or a conveyance accommodating section capable of accommodating each liquid discharged from the collective nozzle head, along the conveyance path.

Here, the "row direction" and the "line direction" do not have to be orthogonal to each other, such as the X direction (transverse direction) and Y direction, and may be diagonal. The collective nozzle head and the individual nozzle head may be independently movable. Moreover, the line and row path conveyance device may have, for example, either a close conveyance path in a rectangular or polygonal shape or the like, or an open conveyance path, as long as it has a line conveyance path and a row conveyance path on the movement path of the nozzle head.

Here, the term "conveyance accommodating section" refers to a portion which accommodates a tip or a liquid in the conveyance device, and preferably has at least conveyance accommodating sections of the same number as that of nozzles of the collective nozzle head.

A seventeenth aspect of the present invention is a carrier treating apparatus, wherein a light receiving device which receives light inside the detached tip-like container or the tube, is provided in a predetermined position along the conveyance path of the line and row path conveyance device.

An eighteenth aspect of the present invention is a method of carrier treatment, comprising: an enclosing step for enclosing a carrier which is capable of adsorbing or capturing a biosubstance in a fluid or is capable of reacting with or binding to the biosubstance, inside a tip-like container comprising; a fitting opening which is fittable to one or a plurality of nozzles for performing gas suction and discharge, or a member to be fitted to the nozzle, and a port through which fluid inflow and outflow can be effected by the gas suction and discharge, and fitting it to a member for use in the suction and discharge mechanism in the fitting opening of the container; and a reaction step for moving the member for fitting the tip-like container for use in the suction and discharge mechanism to a predetermined liquid accommodating section, and reacting by bringing into contact between the filler and a liquid accommodated in a liquid accommodating section by controlling an operation of suction and discharge comprising an amount, a speed, a number of times, a time, and a position of the suction and discharge, according to material conditions including a structure of the nozzle, a member fitted to the nozzle, or the carrier enclosing tip, the type and concentration of a biosubstance in a fluid, the amount of the liquid, the coordinate position including the position of accommodation of the liquid, and the treatment contents.

A nineteenth aspect of the present invention is a method of carrier treatment, wherein the reaction step comprises a measuring step for receiving light from the tip.

A twentieth aspect of the present invention is a method of carrier treatment, wherein the reaction step is performed by sucking a liquid from the tip of the carrier enclosing tip into the carrier enclosing tip.

Effects of the Invention

According to the first aspect of the invention, the carrier can be enclosed in a tip-like container having an opening for fitting to a nozzle capable of precise control for use in gas suction and discharge, or to a member to be fitted to a nozzle such as a tip, and a port, and optimum conditions can be set for the treatment purpose, and suction and discharge with respect to the tip-like container and the carrier. Moreover, a fluid can flow not only in one way, but also in two ways. Accordingly, separation, extraction, purification performance, and treatment efficiency of the carrier can be improved.

Furthermore, suction by selecting an external optional fluid in a state where the carrier is enclosed in the tip-like container, enables contact between the carrier and the fluid. Accordingly, by replacing the treatment of the carrier with relative movement between the carrier enclosing tip and an external container, and control of suction and discharge, the treatment can be automated, generalized, and diversified.

By using the suction and discharge mechanism comprising the carrier enclosing tip enclosing the carrier and the nozzle, the scale of the apparatus can be reduced.

Moreover, according to the present invention, by merely sucking and discharging a fluid while the carrier such as a filler is enclosed in the tip-like container, and moving the tip-like container, the treatment of liquid chromatography such as reaction, washing, temperature control, separation, agitation, dispensation, clarification, isolation, elution, and extraction can be performed, and thus the treatment can be efficiently, quickly, and readily performed.

Furthermore, according to the present invention, by selecting a tip-like container suitable for the speed of the fluid according to the treatment purpose, and the amount of the fluid to be handled, various treatment can be dealt with, and thus there is generality and diversity.

According to the present invention, by using the carrier enclosing tip enclosing the carrier in the tip-like container fitted to the nozzle or a tip or the like fitted to the nozzle, detachment and attachment of the carrier enclosing tip or another dispensing tip with respect to the nozzle or the like, enables carrier treatment with the same nozzle. Accordingly, various treatments can be efficiently and quickly performed.

According to the second aspect of the present invention, the tip-like container is provided so as to have the carrier accommodating tube, and a passage formed narrower than the carrier accommodating tube. Accordingly, various containers and various liquid amounts can be handled, and thus there is generality. Moreover, by using the transition portion between the carrier accommodating tube and the passage, the carrier and the carrier passage prevention member can be latched and reliably held.

According to the third aspect of the present invention, since the carrier is enclosed in the tip-like container by means of the enclosing section, various carriers can be used by using the enclosing section according to these various carriers, and thus there is generality and diversity.

According to the fourth aspect of the present invention, the carrier passage prevention member and the tip-like container are separately provided. Accordingly, by attaching the carrier passage prevention member to the tip-like container, the carrier can be readily enclosed therein. Moreover, if the carrier passage prevention member is detachably attached, the tip-like member can be reused, or a substance absorbed in the carrier can be directly extracted or collected.

According to the fifth aspect of the present invention, a projection projecting from the wall surface of the tip-like container, a slope, or a step is provided as the enclosing section. Accordingly, the production cost can be reduced by reducing the number of parts, and the carrier can be reliably enclosed.

According to the sixth aspect of the present invention, a filler comprising a plurality of particulate carriers is used as the carrier. Accordingly, the carrier can be introduced into the carrier enclosing tip through the port, and thus the handling is easy.

According to the seventh aspect of the present invention, a permeable porous block-shaped filler or a block-shaped filter is used as the carrier. Accordingly, by appropriately setting the size of the block-shaped filler or the block-shaped filter, outflow from the port of the tip-like container can be prevented, and thus there is no need for an enclosing section for preventing outflow, and the tip-like container or the structure inside thereof can be simplified.

Moreover, the block-shaped filler, differing from a particulate filler, is not dispersed in liquid or does not move around therein by suction and discharge of the fluid, and thus the structure is unchanged. Accordingly, separation with an excellent reproducibility can be achieved.

Changing the pore diameter of the block-shaped filler or the block-shaped filter, and the speed of suction and discharge, enable various treatments.

According to the eighth aspect of the present invention, the carrier or the carrier passage prevention member is held by the projection, the slope, or the step. Accordingly, the carrier is held by the tip-like container and reliably enclosed therein.

According to the ninth aspect of the present invention, by supplying the conductive member formed all over, or partially on, the wall of the tip-like container with an electrical current, to generate heat in the conductive member, so as to heat or cool the carrier and a liquid contained in the tip-like container, the temperature for reaction can be controlled.

Accordingly, since a heating device such as a heater is in direct contact with the inside of the tip-like container, as compared to cases where such a heating device is provided outside of the wall of the tip-like container, heat reflection due to the wall can be prevented and the heat can be more efficiently transmitted to the inside of the tip-like container, and thus the thermal efficiency is high and accurate temperature control can be performed.

Furthermore, since the wall of the tip-like container is formed by a conductive member, the thermal efficiency is high and there is no need for providing a heating device larger than necessary such as a metal block on the outside of the tip-like container, and it is sufficient to merely provide the driving device thereof on the outside. Accordingly, the external structure is simplified and the scale of the overall apparatus can be reduced.

Since an optimum temperature increasing/decreasing member can be previously provided on each tip-like container, there is no need for providing a heating device to satisfy various conditions on the outside, and thus there is generality and diversity.

Since the conductive member is in direct contact with the inside of the tip-like container, the temperature of the liquid can be controlled with high accuracy and faithful responsiveness.

By shortening the duration from the time when a signal for heating or cooling the liquid is given to the tip-like container and the conductive member until the liquid temperature is evenly distributed, the treatment can be quickly and efficiently performed.

According to the tenth aspect and the fourteenth aspect of the present invention, by suppressing the volume of a space in the tip-like container formed between the surface of the enclosed carrier and the inner wall surface of the container to an amount of liquid used for the treatment (very small amount), the liquid sucked into the narrow tube and the overall surface of the carrier can be brought into contact, and thus a very small amount of liquid can be handled with high reliability.

According to the eleventh aspect of the present invention, the carrier or the carrier passage prevention member is held in the tip-like container using the slope or step of the transition portion from the narrow tube to the wide tube of the tip-like container. Accordingly, the carrier can be readily and reliably latched and held without any specific processing of the tip-like container.

According to the twelfth aspect of the present invention, by providing at least two separate predetermined projections or the like along the movement path of the fluid linking the fitting opening and the port, carriers of various shapes can be readily enclosed, and thus the handling is easy, and there is generality and diversity. In particular, even a membranous filter or thin plate-shaped filter can be reliably enclosed and attached to allow a fluid to pass smoothly therethrough, and thus gas suction and discharge can readily make a fluid pass through even a filter such as an ultrafiltration membrane having a small pore diameter.

According to the thirteenth aspect and the eighteenth aspect of the present invention, the carrier enclosing tip having the carrier in the tip-like container is fitted to a nozzle or to a member for use in gas suction and discharge such as a tip fitted to the nozzle, and the amount, the speed, the number of times, the time, and the position of suction and discharge with respect to the nozzle are controlled according to the structure of the tip-like container and the like.

Consequently, according to the present invention, by using a carrier enclosing tip having a predetermined structure, and performing delicate control of suction and discharge, treatment such as agitation, washing, and reaction between the carrier enclosed in the tip and a solution containing a predetermined biosubstance can be performed readily, consistently, quickly, and efficiently with high reliability. Moreover, according to the present invention, various treatments can be dealt with by changing the treatment contents, and thus there is generality and diversity.

According to the fifteenth aspect and the nineteenth aspect of the present invention, the temperature is controlled by providing the temperature increasing/decreasing member closer from the outside of the tip-like container of the carrier enclosing tip. Accordingly, the temperature can be controlled while the carrier is enclosed in the tip, and thus various treatments such as enclosure and reaction, up to separation can be consistently performed. Moreover, since the temperature is controlled while the carrier is enclosed, the treatments are efficient and quick.

According to the sixteenth aspect of the present invention, while using an apparatus serving as the nozzle head provided with a plurality of nozzles for performing suction and discharge, and moving at once, a part of the plurality of nozzles is used as the collective nozzles and another part thereof is used as an individual nozzle, and this is used alternatively for exclusive purposes. That is, the apparatus is used while a tip or a tip-like container is fitted to the apparatus in use and a tip and a tip-like container are not fitted to the nozzle not in use. Consequently, the nozzle in use and the nozzle not in use are both subjected to gas suction and discharge at once, however the nozzle not in use does not act on the corresponding container by the suction and discharge. Accordingly, while using an apparatus having a plurality of nozzles which perform suction and discharge at once, suction and discharge can be individually performed with respect to a container on the movement path of each nozzle. Hence various treatments can be performed.

Moreover, according to the present invention, on the movement path of the collective nozzles and the individual nozzle is provided a line and row path conveyance device having a conveyance path provided with the row conveyance path and the line conveyance path. Accordingly, treatment can be performed with either the collective nozzles or the individual nozzle by the conveyance device, and thus various and complicated treatments can be performed in a simple and compact structure using a small number of nozzles without arranging a large number of nozzles and a suction and discharge mechanism in matrix.

Furthermore, when a large number of treatment objects are subjected to suction and discharge treatment, common treatment items are performed collectively using the collective nozzles, and treatment items requiring to be individually performed are performed individually using the individual nozzle, and thereby various treatments can be efficiently and quickly performed.

In particular, the present invention is suitable when measurement is individually performed, in cases where a required reagent is added just before the measurement, or cases where a reagent requiring to be held at a predetermined temperature is added just before individual treatment.

According to the seventeenth aspect and the nineteenth aspect of the present invention, by providing a light receiving device at least in one point on the conveyance path of the line and row path conveyance device, the reaction state of treatment corresponding to respective nozzles or the like treated with a plurality of nozzles or the like, is observed by receiving light, and thereby the reaction result can be reliably understood. Moreover, the measurement can be sequentially performed by using a small number of light receiving devices. Accordingly, the apparatus can be simplified. In particular, reagents required only just before the light reception by means of the light receiving devices can be sequentially placed just before the light reception by the individual nozzle, and thus light can be efficiently received with high reliability. According to the twentieth aspect of the present invention, while the carrier enclosing tip is not detached from the nozzle, but is attached to the nozzle, a liquid can be sucked into a tip and can be brought into contact with the carrier at the same time, and thus the treatment can be efficiently performed.

BEST MODE FOR CARRYING OUT THE INVENTION

The present invention enables the performance of separation/purification with increased efficiency, rapidity, and reliability by enclosing a carrier such as a filler in a tip-like container to use a suction and discharge function, so as to perform highly accurate suction and discharge under a condition where a predetermined amount, speed, time, number of times, and the like of a predetermined fluid, serving as a so-called mobile phase, are set with respect to the tip-like container.

Next is a description of embodiments of the present invention with reference to the drawings. Description of each embodiment is, unless otherwise stated, not to be considered as limiting the present invention.

Figure 1:
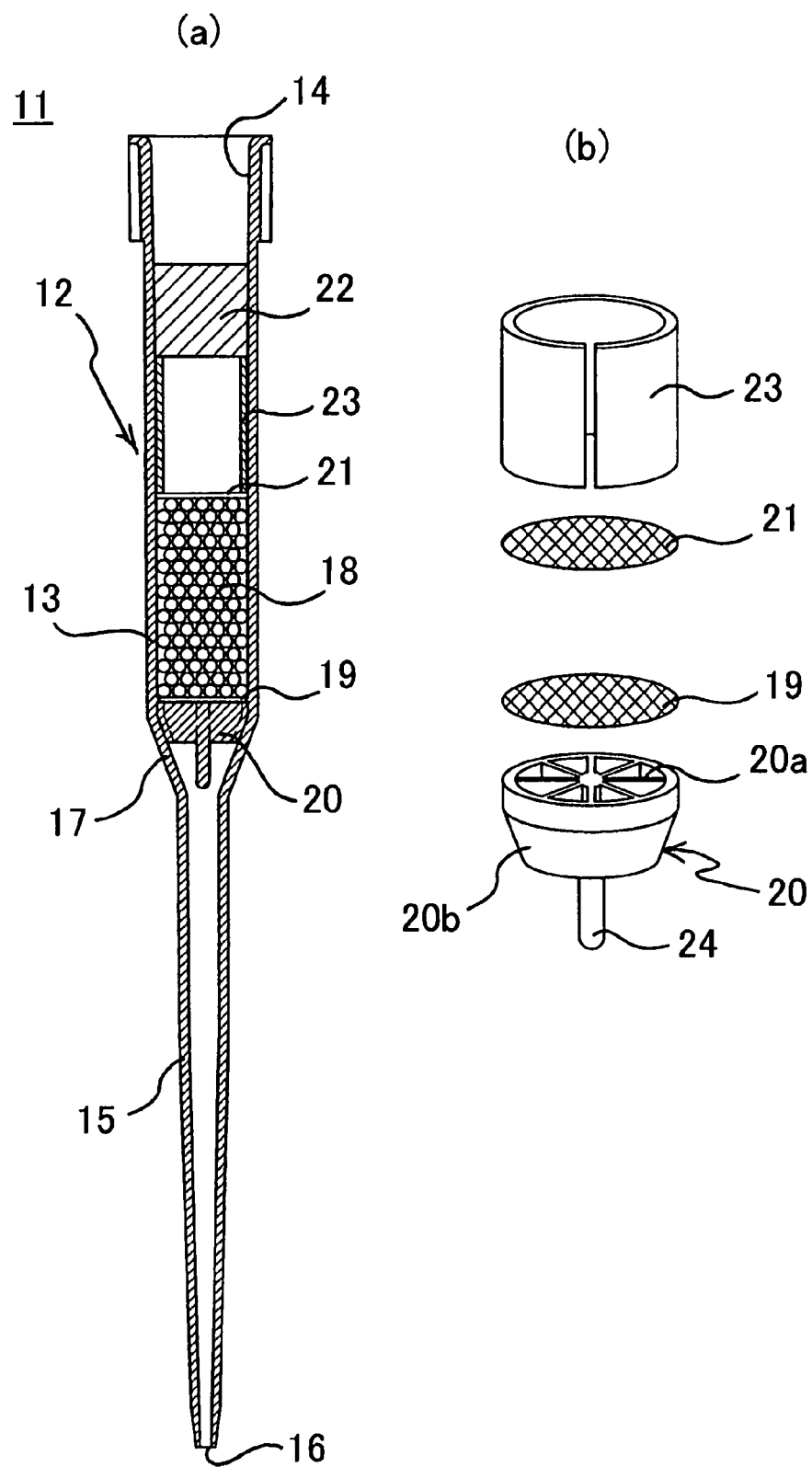
FIG. 1 shows a carrier enclosing tip according to a first embodiment of the present invention.

FIG. 1 shows a cross-sectional view of a carrier enclosing tip 11 according to a first embodiment of the present invention. In the carrier enclosing tip 11, a particulate filler 18 serving as a carrier is enclosed in a tip-like container 12. The tip-like container 12 comprises: a substantially cylindrical large diameter tube 13 serving as a carrier accommodating tube which accommodates the particulate filler 18; a substantially cylindrical small diameter tube 15 which is communicated with the large diameter tube 13, and is formed narrower than the large diameter tube 13 and a nozzle (not shown) to be fitted thereto; and a substantially funnel-shaped transition portion 17 formed between the large diameter tube 13 and the small diameter tube 15.

The upper side of the large diameter tube 13 is provided with a cylindrical fitting opening 14 to be fitted to a nozzle (not shown) where gas suction and discharge is performed, or to a tip fitted to the nozzle. At the tip of the small diameter tube 15 is provided a port 16 through which fluid inflow and outflow can be effected by gas suction and discharge with the nozzle. The particulate filler 18 is accommodated in the large diameter tube 13 serving as the carrier accommodating tube. The diameter of each particle of the particulate filler 18 is, for example, about several micrometers such as 5 µm, 2 µm, and 3 µm. The lower side and the upper side of a portion where the particulate filler 18 is accommodated, are provided with mesh-like thin plates 19 and 21, as carrier passage prevention members of the enclosing section, whose holes are smaller than the particle diameter, so as to sandwich the particulate filler 18. The mesh-like thin plate 19 provided on the lower side is attached to the tip-like container 12 by a thin plate holding section 20 in a substantially truncated conic shape which engages with the transition portion 17. The thin plate holding section 20 comprises: a substantially funnel-shaped engagement tube 20b which engages with the transition portion 17; a shaft 24 which is formed projecting downward from the engagement tube 20b along the central axis direction of the engagement tube 20b, for guiding a discharged fluid along the central axis; and a plurality of plate-shaped ribs 20a extending radially toward the shaft 24.

Furthermore, on the upper side of the mesh-like thin plate 21 that is provided on the upper side of the particulate filler 20, is provided a radially and elastically energized C-shaped spacer 23, so that a space between the mesh-like thin plate 21 and an air filter 22 provided thereon is kept constant.

Figure 2:
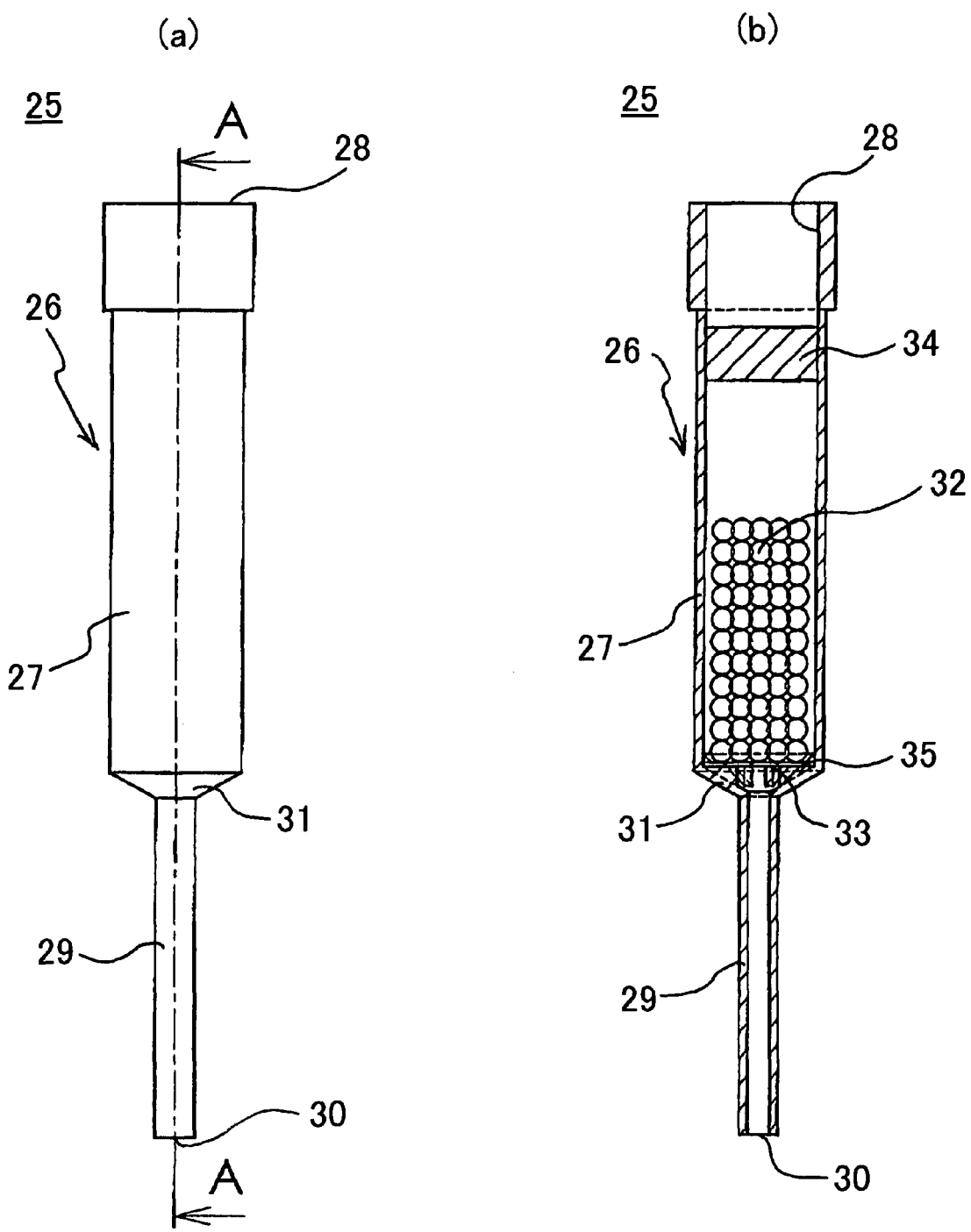
FIG. 2 shows a carrier enclosing tip according to a second embodiment of the present invention.

FIG. 2 shows a carrier enclosing tip 25 according to a second embodiment of the present invention. In the carrier enclosing tip 25, a particulate filler 32 serving as a carrier is enclosed in a tip-like container 26. The tip-like container 26 comprises: a substantially cylindrical large diameter tube 27 serving as a carrier accommodating tube which accommodates the particulate filler 32; a substantially cylindrical small diameter tube 29 which is communicated with the large diameter tube 27, and is formed narrower than the large diameter tube 27 and a nozzle (not shown) to be fitted thereto; and a substantially funnel-shaped transition portion 31 provided between the large diameter tube 27 and the small diameter tube 29.

The upper side of the large diameter tube 27 is provided with a cylindrical fitting opening 28 to be fitted to a nozzle (not shown) where gas suction and discharge is performed, or to a tip fitted to the nozzle. At the tip of the small diameter tube 29 is provided a port 30 through which fluid inflow and outflow can be effected by gas suction and discharge with the nozzle. The particulate filler 32 is accommodated in the large diameter tube 27 corresponding to the carrier accommodating tube. The diameter of each particle of the particulate filler 32 is, for example, in the same manner as that of the particulate filler 18 according to the first embodiment, about several micrometers such as 5 μm, 2 μm, and 3 μm. The lower side portion where the particulate filler 32 is accommodated, is provided with a mesh-like thin plate 35, serving as a carrier passage prevention member of the enclosing section, whose holes are smaller than the particle diameter. The mesh-like thin plate 35 is provided so as to be supported on the transition portion 31, and so as to partition between the fitting opening 28 and the port 30. On the lower side of the mesh-like thin plate 35 is provided a plurality of plate-shaped ribs 33 so as to be in contact with the inner wall of the transition portion 31. Moreover, on the upper side of the large diameter tube 27 is provided an air filter 34 through which a gas can pass, so as to partition between the fitting opening 28 and the port 30.

Figure 3:
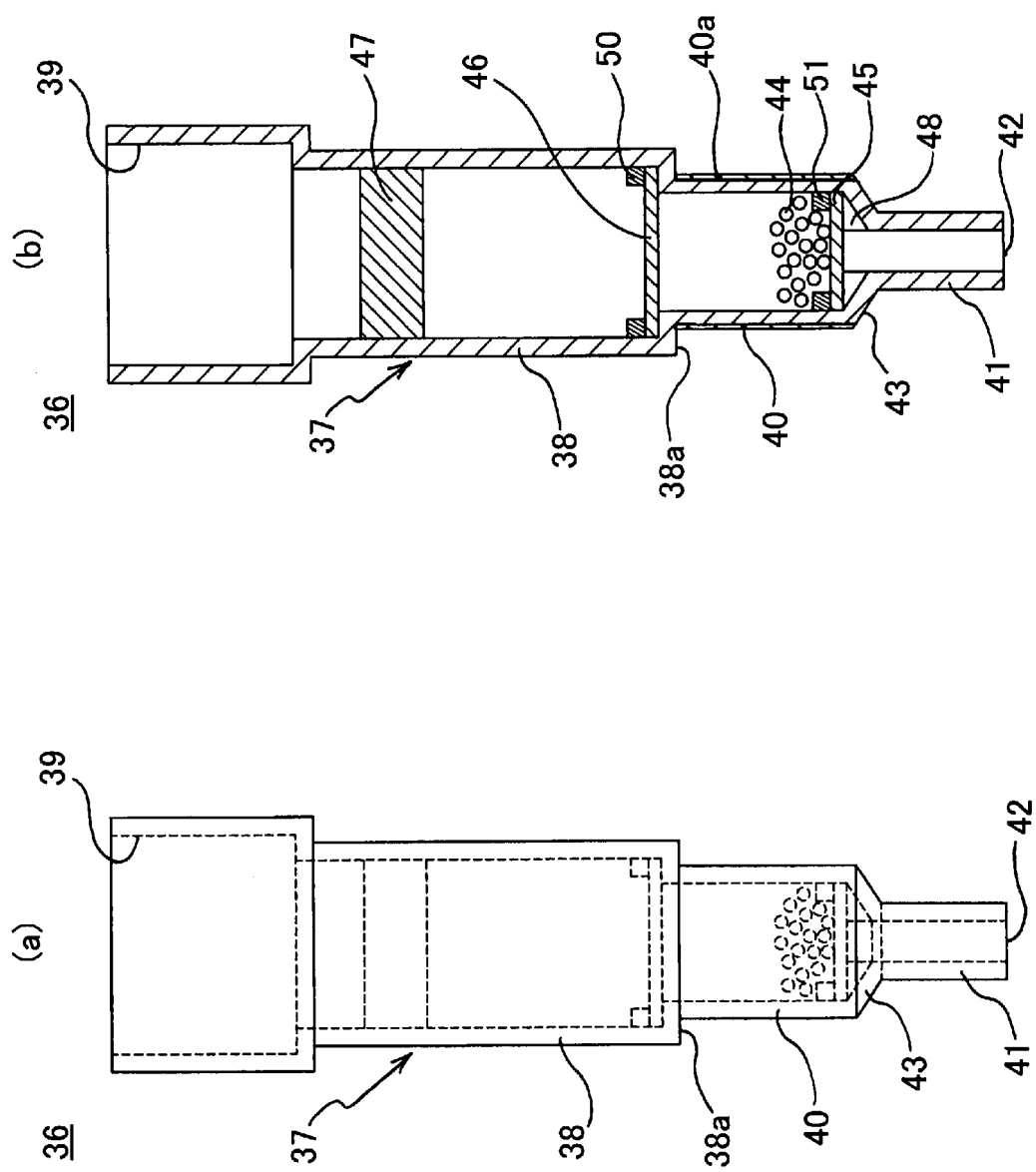
FIG. 3 shows a carrier enclosing tip according to a third embodiment of the present invention.

FIG. 3 shows a carrier enclosing tip 36 according to a third embodiment of the present invention. In the carrier enclosing tip 36, a particulate filler 44 serving as a carrier is enclosed in a tip-like container 37. The tip-like container 37 comprises: a substantially cylindrical large diameter tube 40 serving as a carrier accommodating tube which accommodates the particulate filler 44; a largest diameter tube 38 which is communicated with the upper side of the large diameter tube 40; a small diameter tube 41 which is communicated with the lower side of the large diameter tube 40; a step 38a formed between the large diameter tube 40 and the largest diameter tube 38; and a substantially funnel-shaped transition portion 43 formed between the large diameter tube 40 and the small diameter tube 41. Here, the largest diameter tube 38 corresponds to the storage tube, and is used to temporarily store an introduced fluid.

The upper side of the largest diameter tube 38 is provided with a cylindrical fitting opening 39 which is fittable to a nozzle (not shown) or to a tip fitted to the nozzle. At the tip of the small diameter tube 41 is provided a port 42 through which fluid inflow and outflow can be effected by gas suction and discharge with the nozzle. The particulate filler 44 is accommodated in the large diameter tube 40 serving as the carrier accommodating tube. The diameter of each particle of the particulate filler 44 is the same as that of the particulate filler 18 according to the first embodiment and the particulate filler 32 according to the second embodiment.

The lower side of a portion where the particulate filler 44 is accommodated, is provided with a mesh-like thin plate 45, serving as a carrier passage prevention member of the enclosing section, whose holes are smaller than the particle diameter. The mesh-like thin plate 45 is provided so as to be supported on the transition portion 43, and so as to partition between the fitting opening 39 and the port 42. On the lower side of the mesh-like thin plate 45 is provided a plurality of plate-shaped ribs 48 so as to be in contact with the inner wall of the transition portion 43. Moreover, on the step 38a between the large diameter tube 40 and the largest diameter tube 38 is provided a mesh-like thin plate 46 serving as a carrier passage prevention member of the enclosing section, whose holes are smaller than the particle diameter, and which is provided in the largest diameter tube 38 to partition between the fitting opening 39 and the port 42. Furthermore, on the upper side of the largest diameter tube 38 is provided an air filter 47 through which a gas can pass, so as to partition between the fitting opening 39 and the port 42. According to the present embodiment, by providing the largest diameter tube 38, a large volume of fluid exceeding the capacity of the large diameter tube 40 or the small diameter tube 41 can be in contact with the particulate filler 44.

Moreover, as shown in FIG. 3(b), the outer wall of the large diameter tube 40 of the tip-like container 37 is covered with a conductive thin membrane 40a. The temperature can be controlled by bringing an electrode into contact with the conductive thin membrane 40a and supplying an electrical current thereto.

Figure 4:
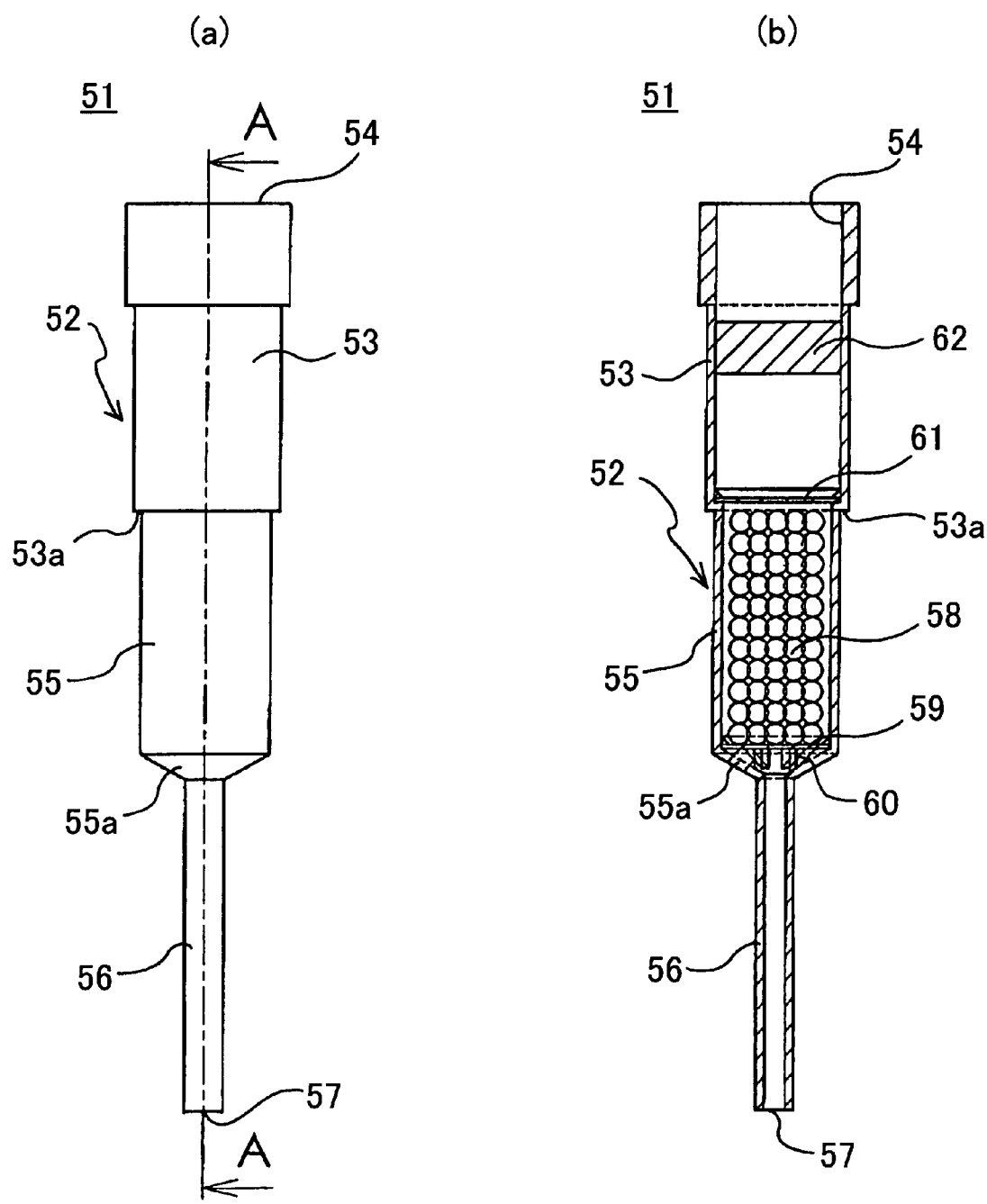
FIG. 4 shows a carrier enclosing tip according to a fourth embodiment of the present invention.

FIG. 4 shows a carrier enclosing tip 51 according to a fourth embodiment of the present invention. In the carrier enclosing tip 51, a particulate filler 58 serving as a carrier is enclosed in a tip-like container 52. The tip-like container 52 comprises: a large diameter tube 55 serving as a carrier accommodating tube which accommodates the particulate filler 58; a largest diameter tube 53 which is communicated with the upper side of the large diameter tube 55; a small diameter tube 56 which is communicated with the lower side of the large diameter tube 55; a step 53a formed between the large diameter tube 55 and the largest diameter tube 53; and a substantially funnel-shaped transition portion 55a formed between the large diameter tube 55 and the small diameter tube 56. The largest diameter tube 53 is used to temporarily store a fluid introduced from a port 57 described later.

The upper side of the largest diameter tube 53 is provided with a cylindrical fitting opening 54 which is fittable to a member used for a suction and discharge mechanism where gas suction and discharge is performed, such as a nozzle (not shown), or a tip fitted to the nozzle. At the tip of the small diameter tube 56 is provided a port 57 through which fluid inflow and outflow can be effected by gas suction and discharge with the nozzle. The particulate filler 58 is accommodated in the large diameter tube 55 serving as the carrier accommodating tube. The diameter of each particle of the particulate filler 58 is the same as that of the particulate filler 18 according to the first embodiment, the particulate filler 32 according to the second embodiment, and the particulate filler 44 according to the third embodiment. The lower side of a portion where the particulate filler 58 is accommodated so as to substantially fill inside the large diameter tube 55, is provided with a permeable porous thin plate 59 serving as a carrier passage prevention member of the enclosing section, whose holes are smaller than the particle diameter.

The permeable porous thin plate 59 is provided so as to be supported on the transition portion 55a, and so as to partition between the fitting opening 54 and the port 57. On the lower side of the permeable porous thin plate 59 is provided a plurality of plate-shaped ribs 60 so as to be in contact with the inner wall of the transition portion 55a. Moreover, on the step 53a between the large diameter tube 55 and the largest diameter tube 53 is provided a permeable porous thin plate 61 serving as a carrier passage prevention member of the enclosing section, whose holes are smaller than the particle diameter, and which is provided on the largest diameter tube 53 to partition between the fitting opening 54 and the port 57. Furthermore, on the upper side of the largest diameter tube 53 is provided an air filter 62 through which a gas can pass so as to partition between the fitting opening 54 and the port 57. By so doing, a large volume of fluid exceeding the capacity of the large diameter tube 55 or the small diameter tube 56 can be in contact with the particulate filler 58.

Figure 5:
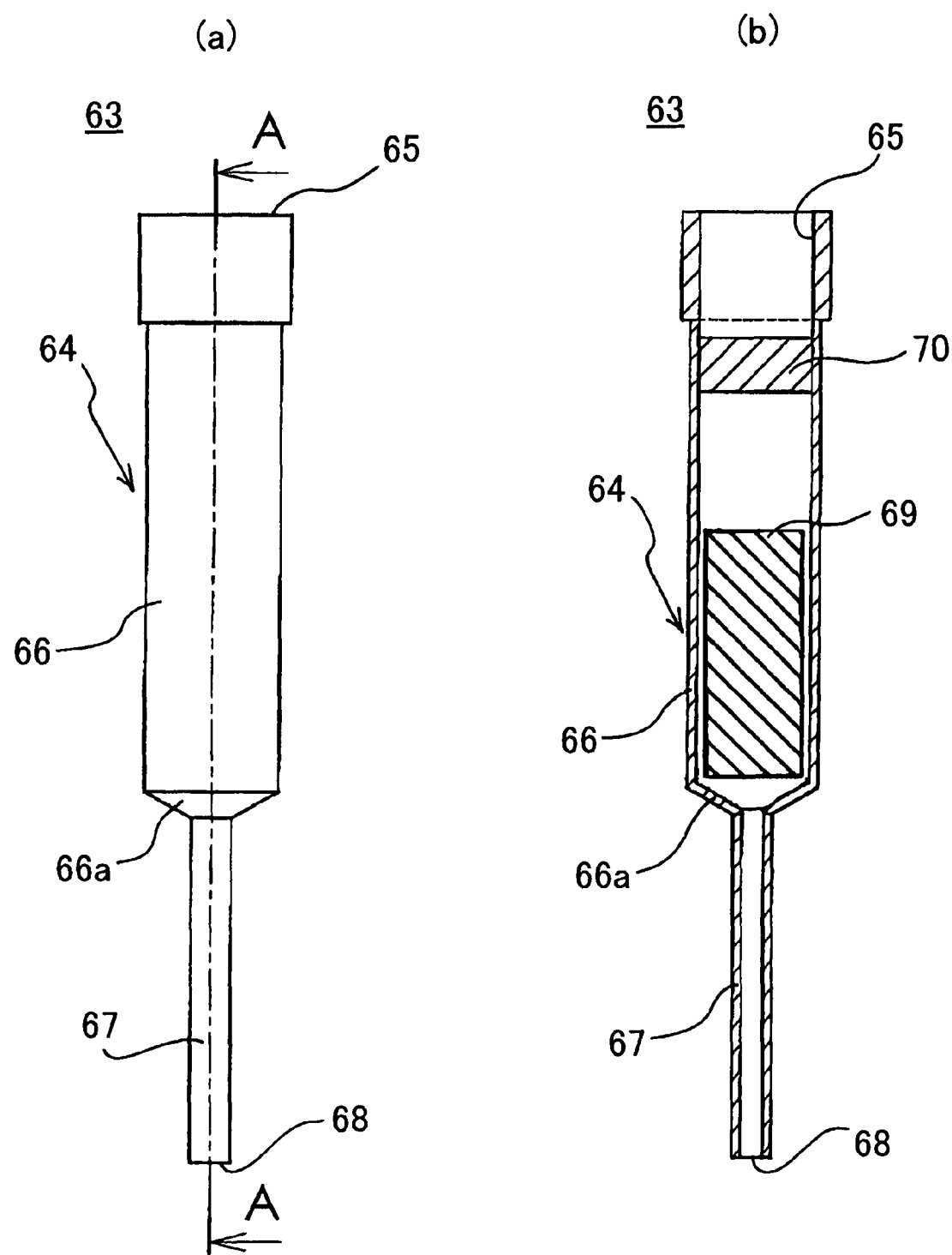
FIG. 5 shows a carrier enclosing tip according to a fifth embodiment of the present invention.

FIG. 5 shows a carrier enclosing tip 63 according to a fifth embodiment of the present invention. In the carrier enclosing tip 63, a substantially cylindrical permeable porous block-shaped filler 69 serving as a carrier is enclosed in a tip-like container 64. The tip-like container 64 comprises: a substantially cylindrical large diameter tube 66 serving as a carrier accommodating tube which accommodates the block-shaped filler 69; a substantially cylindrical small diameter tube 67 which is communicated with the large diameter tube 66, and is formed narrower than the large diameter tube 66 and a nozzle (not shown) to be attached thereto, or the large diameter tube 66; and a substantially funnel-shaped transition portion 66a provided between the large diameter tube 66 and the small diameter tube 67.

The upper side of the large diameter tube 66 is provided with a cylindrical fitting opening 65 which is fittable to a nozzle (not shown) or to a tip fitted to the nozzle. At the tip of the small diameter tube 67 is provided a port 68 through which fluid inflow and outflow can be effected by gas suction and discharge with the nozzle. The block-shaped filler 69 is accommodated in the large diameter tube 66 serving as the carrier accommodating tube. The block-shaped filler 69 is formed in a size which does not pass through the small diameter tube 67.

Here, the permeable porous block-shaped filler 69 has a structure in which a three-dimensional network skeleton and its voids are integrated. The skeleton size and the passage size can be independently determined. By increasing the passage size as compared with the size of a particulate filler, suction and discharge can be performed at a lower pressure.

Furthermore, on the upper side of the large diameter tube 66 is provided an air filter 70 through which a gas can pass, so as to partition between the fitting opening 65 and the port 68. Although an enclosing section is not provided in the present example, there may be provided, for example, two mesh-like thin plates so as to sandwich the block-shaped filler 69 from the top and the bottom and attach it inside the large diameter tube 66.

Figure 6:
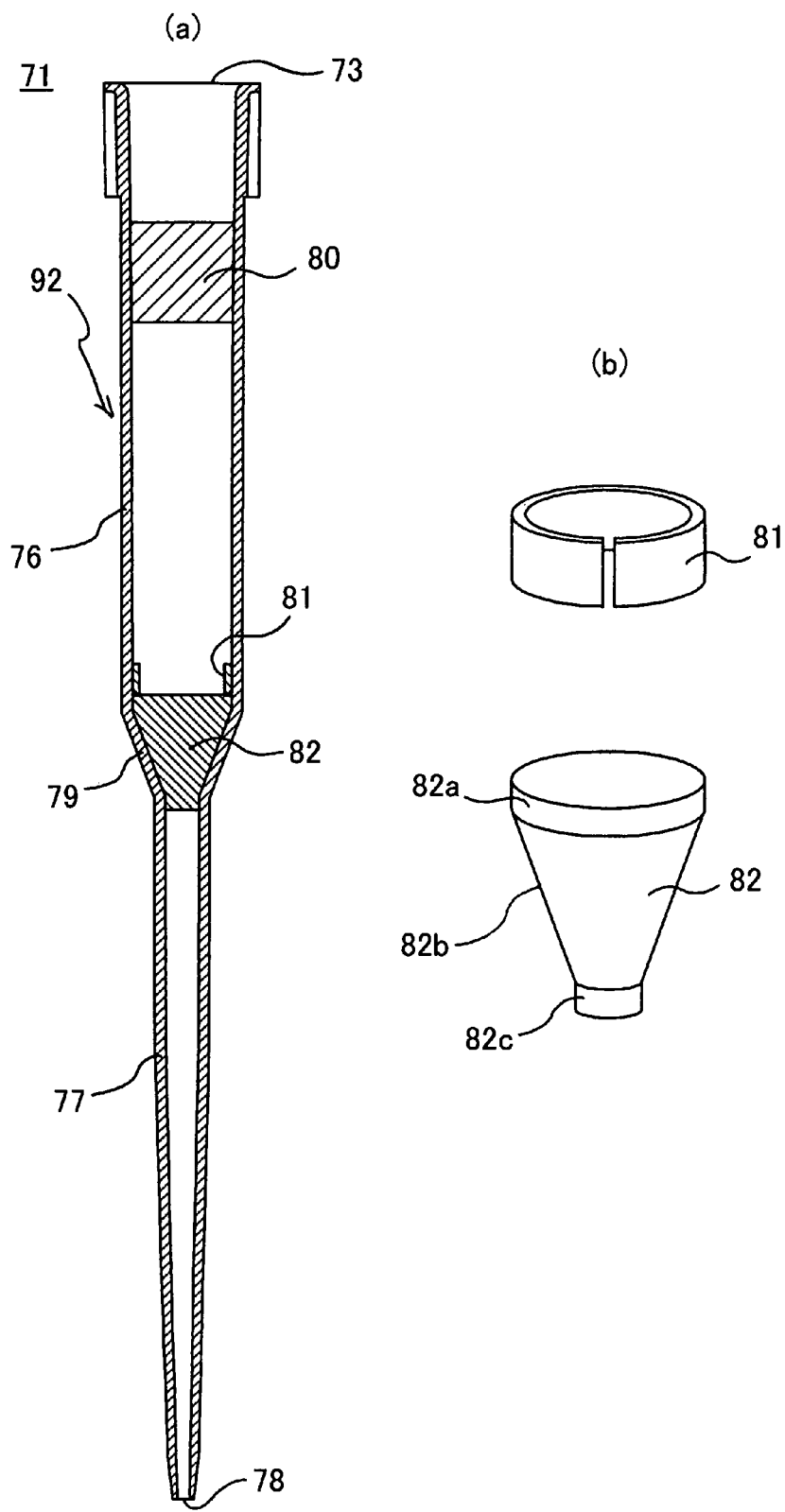
FIG. 6 shows a carrier enclosing tip according to a sixth embodiment of the present invention.

FIG. 6 shows a carrier enclosing tip 71 according to a sixth embodiment. In the carrier enclosing tip 71, a substantially truncated conic permeable porous block-shaped filter 82 serving as a carrier is enclosed in a tip-like container 72. The tip-like container 72 comprises: a substantially cylindrical large diameter tube 76 which corresponds to the storage tube; a substantially cylindrical small diameter tube 77 which is communicated with the large diameter tube 76, and is formed narrower than the large diameter tube 76 and a nozzle (not shown) to be fitted thereto; and a substantially funnel-shaped transition portion 79 serving as a carrier accommodating tube which accommodates the block-shaped filter 82, that is provided between the large diameter tube 76 and the small diameter tube 77.

The upper side of the large diameter tube 76 is provided with a cylindrical fitting opening 73 which is fittable to a nozzle (not shown) or to a tip fitted to the nozzle. At the tip of the small diameter tube 77 is provided a port 78 through which fluid inflow and outflow can be effected by gas suction and discharge with the nozzle. On the upper side of the large diameter tube 76 which corresponds to the storage tube, is provided an air filter 80 through which a gas can pass.

The transition portion 79 serving as a carrier accommodating tube, is provided with the block-shaped filter 82 so as to engage therewith. The block-shaped filter 82 comprises: a column-shaped large diameter engagement portion 82a which engages with the large diameter tube 76; a truncated conic transition portion engagement portion 82b which engages with the transition portion 79; and a column-shaped small diameter engagement portion 82c which engages with the small diameter tube 77. The upper side of the block-shaped filter 82 is pressed by a radially and elastically energized C-shaped ring 81.

Here, the enclosing section corresponds to the substantially funnel-shaped transition portion 79 and the ring 81 serving as a carrier passage prevention member.

Figure 7:
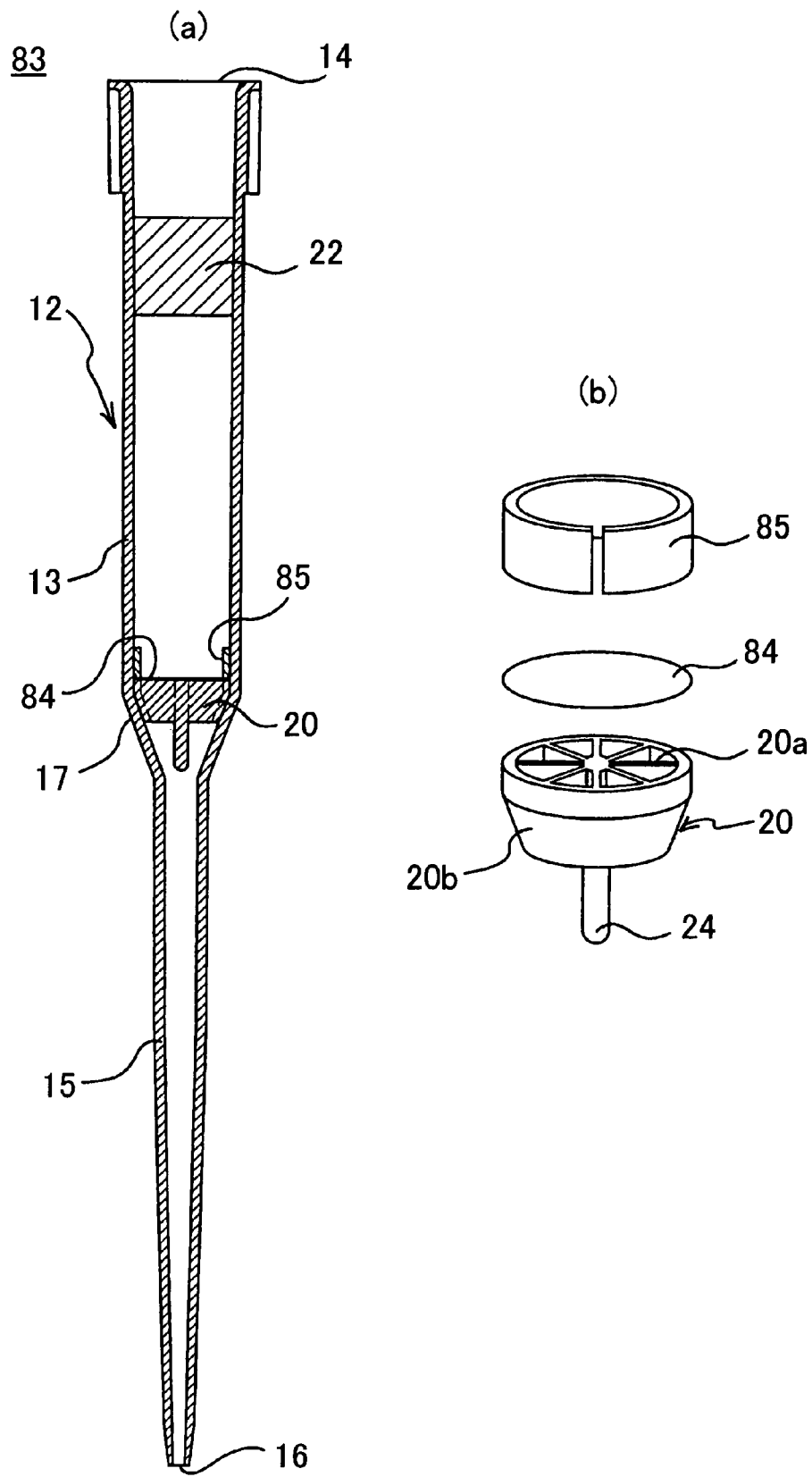
FIG. 7 shows a carrier enclosing tip according to a seventh embodiment of the present invention.

A carrier enclosing tip 83 according to a seventh embodiment is shown based on FIG. 7. In the carrier enclosing tip 83, a thin membranous filter 84 serving as a carrier is enclosed in the abovementioned tip-like container 12 according to the first embodiment. The same reference symbols are used for components the same as those described in FIG. 1. The tip-like container 12 comprises: the substantially cylindrical large diameter tube 13 which corresponds to the storage tube; the substantially cylindrical small diameter tube 15 which is communicated with the large diameter tube 13, and is formed narrower than the large diameter tube 13 and a nozzle (not shown) to be fitted thereto; and the substantially funnel-shaped transition portion 17 serving as a carrier accommodating tube which accommodates the thin membranous filter 84, that is provided between the large diameter tube 13 and the small diameter tube 15.

The upper side of the large diameter tube 13 is provided with the cylindrical fitting opening 14 which is fittable to a nozzle (not shown) or to a tip fitted to the nozzle. At the tip of the small diameter tube 15 is provided the port 16 through which fluid inflow and outflow can be effected by gas suction and discharge with the nozzle. On the upper side of the large diameter tube 13 which corresponds to the storage tube, is provided an air filter 22 through which a gas can pass.

The transition portion 17 serving as a carrier accommodating tube is provided with the thin membranous filter 84 so as to partition between the fitting opening 14 and the port 16. On the lower side of the thin membranous filter 84 is provided the substantially truncated conic thin plate holding section 20 which engages with the transition portion 17, to be thereby attached to the tip-like container 12. The thin plate holding section 20 is the same as described above, and thus the description thereof is omitted.

Furthermore, on the upper side of the thin membranous filter 84 is provided a radially and elastically energized C-shaped ring 85 for pressing the thin membranous filter 84.

Figure 8:
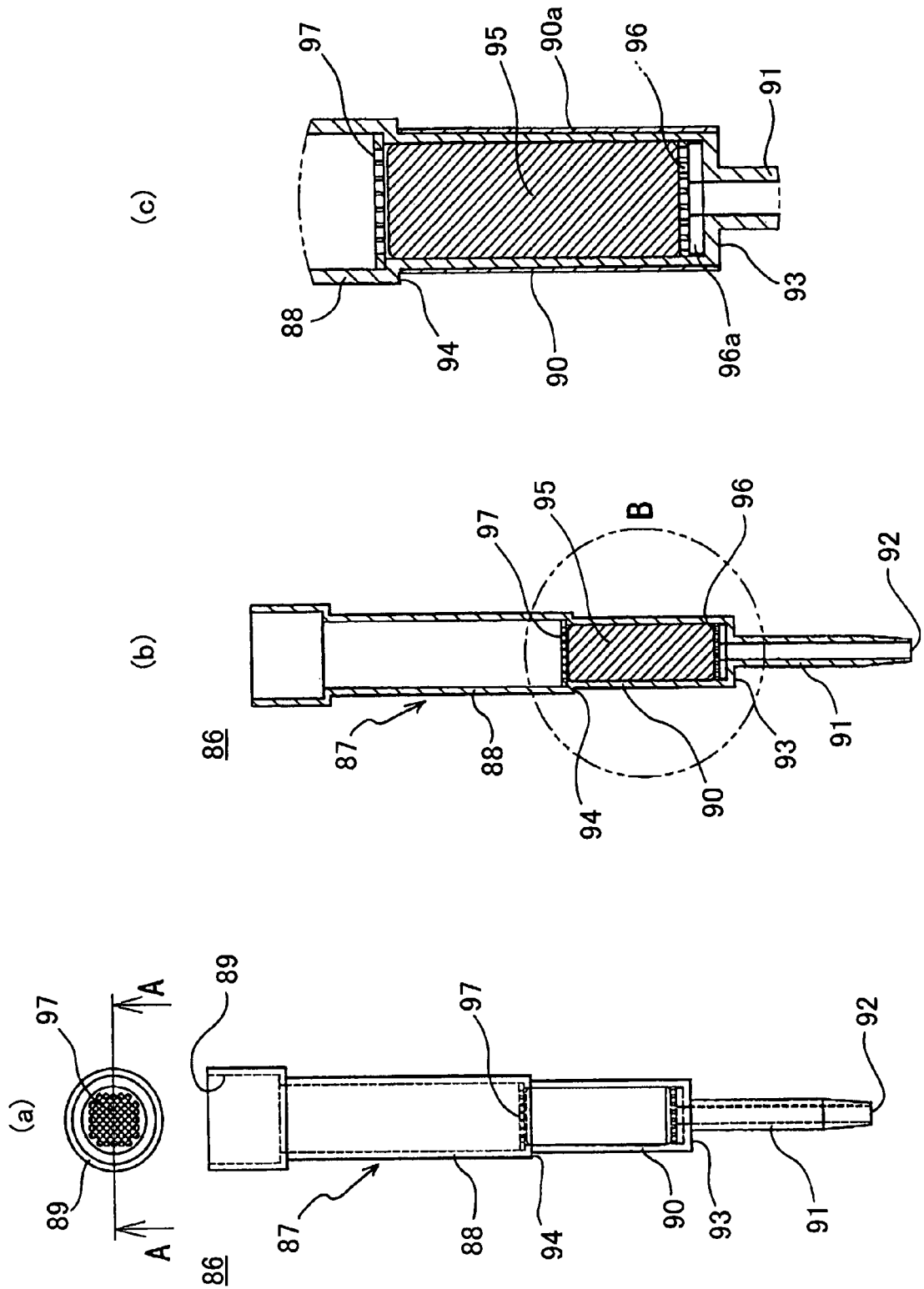
FIG. 8 shows a carrier enclosing tip according to an eighth embodiment of the present invention.

FIG. 8 shows a carrier enclosing tip 86 according to an eighth embodiment of the present invention. As shown in FIG. 8(a), and in FIG. 8(b) which shows a cross-section taken along the line AA thereof, in the carrier enclosing tip 86, a cylindrical permeable porous block-shaped filter 95 serving as a carrier is enclosed in a tip-like container 87. The tip-like container 87 comprises: a substantially cylindrical largest diameter tube 88 which corresponds to the storage tube; a large diameter tube 90 which is communicated with the largest diameter tube 88, is formed narrower than the largest diameter tube 88, and corresponds to the carrier accommodating tube which accommodates the block-shaped filter 95 substantially tightly by having substantially the same size and shape; a substantially cylindrical small diameter tube 91 which is formed further narrower than the large diameter tube 90; a step 94 provided between the largest diameter tube 88 and the large diameter tube 90; and a step 93 serving as a transition portion which is provided between the small diameter tube 91 and the large diameter tube 90.

The upper side of the largest diameter tube 88 is provided with a cylindrical fitting opening 89 which is fittable to a nozzle (not shown) or to a tip fitted to the nozzle where gas suction and discharge is performed. At the tip of the small diameter tube 91 is provided a port 92 through which fluid inflow and outflow can be effected by gas suction and discharge with the nozzle.

As shown in FIG. 8(c) which is an enlarged view of the part B in FIG. 8(b), on the lower side of the block-shaped filter 95 is provided a permeable porous thin plate 96 serving as a member for enclosing and fixing the block-shaped filter 95. Thin plate-shaped ribs 96a are provided on the lower side of the thin plate 96 to prevent clogging of holes in the thin plate 96, and are latched and held on the step 93. Furthermore, on the upper side of the block-shaped filter 95 is provided a permeable porous thin plate 97 by being latched by the step 94 between the largest diameter tube 88 and the large diameter tube 90, to fix and enclose the block-shaped filter 95 in the large diameter tube 90. Moreover, the outer wall of the large diameter tube 90 is covered with a conductive thin membrane 90a. The temperature can be controlled by bringing an electrode into contact with the conductive thin membrane 90a and supplying an electrical current thereto.

Figure 9:
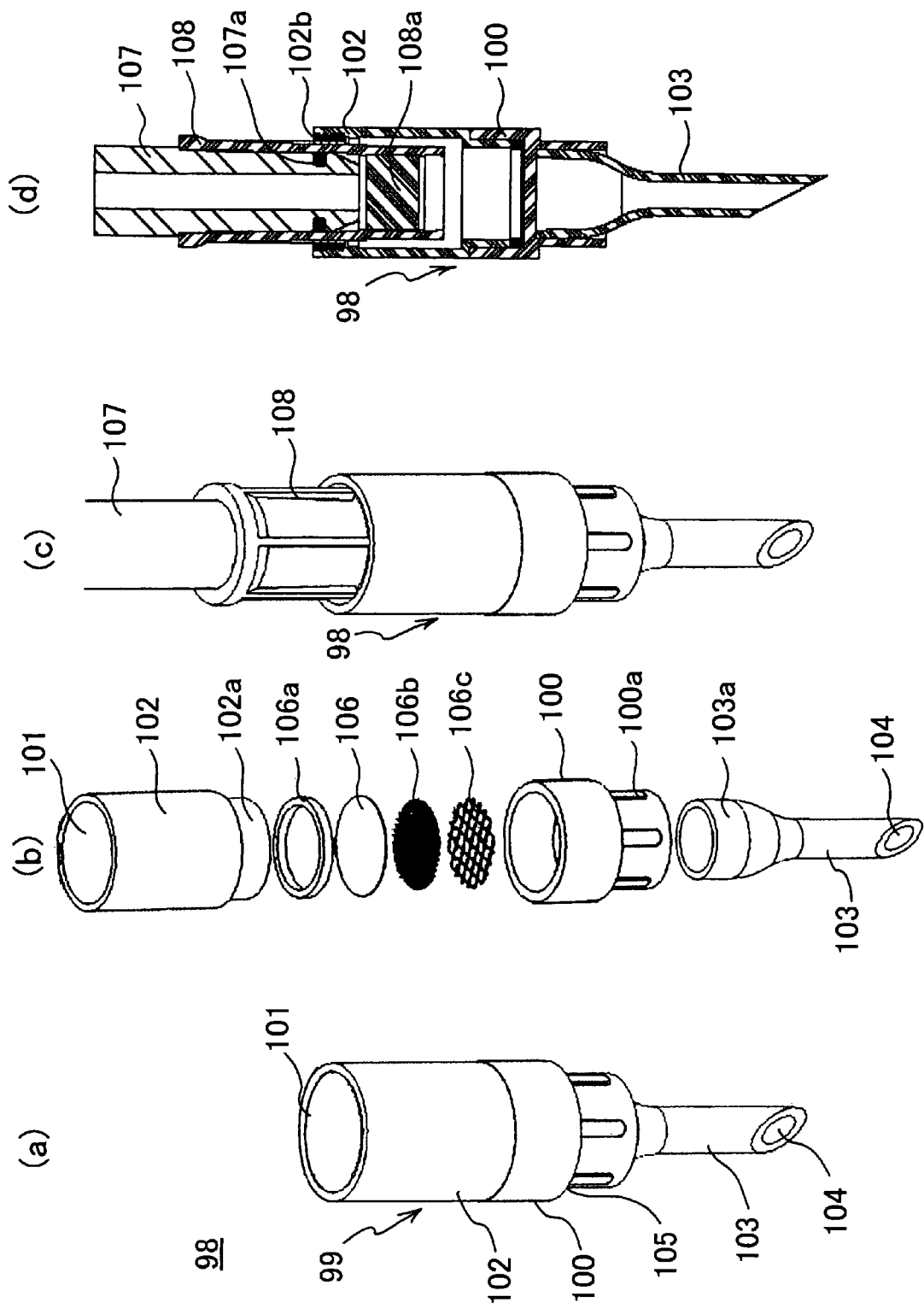
FIG. 9 shows a carrier enclosing tip according to a ninth embodiment of the present invention.

FIG. 9 shows a carrier enclosing tip 98 according to a ninth embodiment of the present invention. In the carrier enclosing tip 98, a thin membranous filter 106 serving as a carrier is enclosed in a tip-like container 99. The tip-like container 99 comprises: a lower side large diameter tube 100 and an upper side large diameter tube 102 which correspond to the storage tube and which are provided in a mutually detachable manner; a small diameter tube 103 which is formed narrower than the large diameter tubes 100 and 102, and is detachably provided on the lower side large diameter tube 100; and a step 105 serving as a transition portion provided on the lower side large diameter tube 100.

Moreover, as shown in FIG. 9(c) and FIG. 9 (d), the upper side large diameter tube 102 is provided with a fitting opening 101 which is fittable to a nozzle 107 where gas suction and discharge is performed, or a cap-shaped adaptor 108 for preventing cross contamination, which is fitted to the nozzle 107. Furthermore, at the tip of the small diameter tube 103 is formed a port 104 through which fluid inflow and outflow can be effected by gas suction and discharge with the nozzle 107, so as to have a slope inclined relative to the axial direction.

FIG. 9(b) shows an exploded perspective view of the carrier enclosing tip 98. The upper side large diameter tube 102 of the carrier enclosing tip 98 has an engagement tube 102a which is formed slightly narrower than the mainbody of the upper side large diameter tube 102 so as to be fitted in the lower side large diameter tube 100 in engagement. There is a clearance between the end of the engagement tube 102a and the inner bottom of the step 105 provided on the large diameter tube 100, where the following members are inserted; namely, a rubber O ring 106a which elastically energizes a thin membranous filter 106 serving as the carrier, from the top, the thin membranous filter 106 having a predetermined pore size serving as the carrier, a mesh-like thin plate 106b having a slightly larger pore size than the above pore size, which is mainly used for supporting the thin membranous filter 106 without looseness, and a mesh-like thin plate 106c which is provided under the mesh-like thin plate 106b and has a larger pore size than that of the mesh-like thin plate 106b so as to prevent clogging of the thin membranous filter 106. These thin membranous filter 106, and the mesh-like thin plates 106b and 106c are provided so as to partition between the fitting opening 101 and the port 104. Here, for example the thin membranous filter 106 is an ultrafiltration membrane, the mesh-like thin plate 106b is made from a stainless steel having a mesh diameter of about 50 μm, and the mesh-like thin plate 106c is made from a stainless steel having a mesh density of about 40 m/s.

FIGS. 9(c) and (d) show a perspective view of the fitting opening 101 fitted with a nozzle 107 via the tubular adaptor 108, and a cross-sectional view thereof. The nozzle 107 is fitted in the adaptor 108 in engagement. In the adaptor 108 is provided an air filter 108a through which gas can pass, and the end of the nozzle 107 is fitted either close to or in contact with the upper end of the air filter 108a or a mesh-like thin plate to which the air filter 108a is attached. In the vicinity of the end of the nozzle 107 is provided an O ring 107a to prevent gas leakage.

The adaptor 108 is elastically energized by a rubber O ring 102b provided in the vicinity of the opening on the upper side of the fitting opening 101, and is fitted to the fitting opening 101 in engagement.

Figure 10:
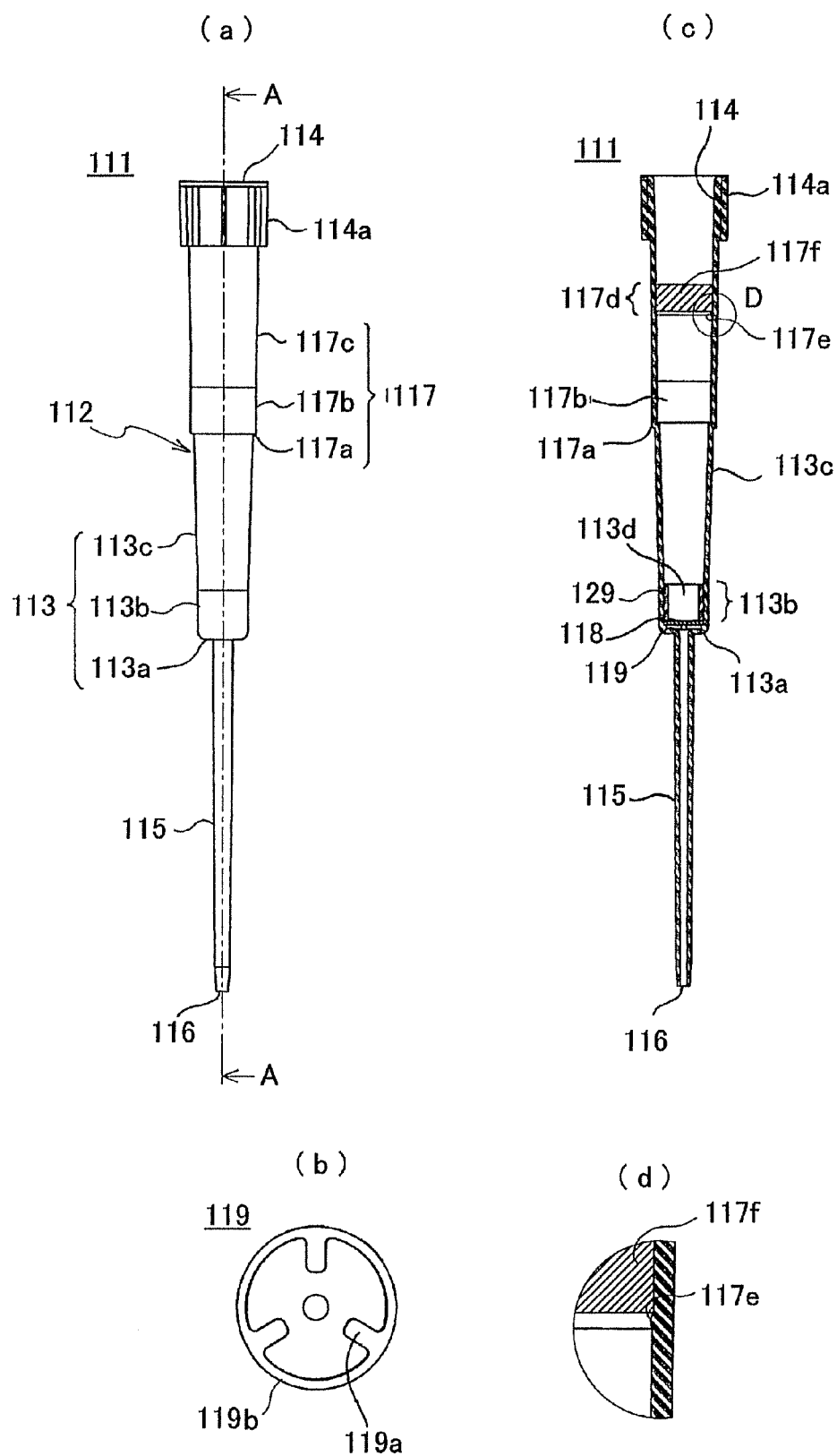
FIG. 10 shows a carrier enclosing tip according to a tenth embodiment of the present invention.

FIG. 10 shows a carrier enclosing tip 110 according to a tenth embodiment of the present invention. As shown in FIG. 10(a), in the carrier enclosing tip 110, a membranous filter, a thin plate-shaped filter, or a thin membranous filter 118 (such as an ultrafiltration membrane) serving as a carrier is enclosed in a tip-like container 112. The tip-like container 112 comprises: a large diameter tube 113; a largest diameter tube 117 which is communicated with the upper side of the large diameter tube 113; and a small diameter tube 115 which is communicated with the lower side of the large diameter tube 113.

The large diameter tube 113 comprises: a step 113a formed between the large diameter tube 113 and the small diameter tube 115; a lower side cylindrical region 113b in which the thin membranous filter 118 is accommodated by being supported on the step 113a; and an inclined cylindrical region 113c which is capable of accommodating a particulate carrier (not accommodating anything in this example), provided on the upper side, and slightly tapered downward.

The largest diameter tube 117 comprises: a step 117a formed between the large diameter tube 113 and the largest diameter tube 117; a lower side cylindrical region 117b which is capable of accommodating the thin membranous filter (not accommodating anything in this example) by being supported on the step 117a; and an inclined cylindrical region 117c which is provided on the upper side and is slightly tapered downward. The upper side of the inclined cylindrical region 117c is provided with a fitting opening 114 which is fittable to a nozzle (not shown).

FIG. 10(c) shows a cross-section taken along the line AA of FIG. 10(a). As shown in FIG. 10(c), around the middle of the inclined cylindrical region 117c is provided an annular projection 117e serving as the projection along a direction orthogonal to the axial direction along the inner wall surface (see FIG. 10(d)). There is a cylindrical region 117d immediately above the annular projection 117e, and an air filter 117f through which air can pass is provided by being supported on the annular projection 117e. Reference symbol 114a denotes a plurality of ribs provided on the outer surface of the upper side of the largest diameter tube 117 along the axial direction thereof.

At the tip of the small diameter tube 115 is provided a port 116 through which fluid inflow and outflow can be effected by gas suction and discharge with the nozzle. Accordingly, the tip-like container of the carrier enclosing tip 111 according to the tenth embodiment is provided with three members, namely: steps 113a and 117a which are provided projecting inward and facing away from the port; and the annular projection 117e serving as the projection which projects inward, so that the inner wall surface thereof is partitioned between the fitting opening 114 and the port 116, in a mutually separated manner in a direction linking the fitting opening 114 and the port 116.

Furthermore, as shown in FIG. 10(b), in the present embodiment, on an the inner bottom face portion 119 on the step 113a is provided: a rim 119b which is provided so as to be in contact with the inner wall surface of the cylindrical region 113b and to surround the axial line of the cylindrical region 113b; and three projections 119a radially projecting from the rim 119b towards the axial line. Thus the thickness of the step is not even. The inner bottom face portion 119 may be provided as a thin plate-shaped spacer member separately from the tip-like container. By so doing, the usable area of the thin membranous filter 118 can be increased.

The thin membranous filter 118 serving as the carrier is provided in contact with the upper side of the inner bottom face portion 119, so as to partition between the fitting opening 114 and the port 116. When the rigidity of the thin membranous filter 118 is low, the thin membranous filter 118 is provided on a supporting mesh-like member (first other enclosing section) mounted on the inner bottom face portion 119.

Furthermore, on the upper side thereof is provided a cylindrical sleeve 129 serving as a carrier passage prevention member serving as the second other enclosing section so as to press a rim portion of the thin membranous filter 118, and therefore the rim 119b. The sleeve 129 may be provided on an O ring placed on the rim portion of the thin membranous filter 118. The membranous filter may also be supported by utilizing the step 117a on the lower end of the largest diameter tube 117 so as to sandwich the filter using an enclosing section as mentioned above.

In the largest diameter tube 117, the lower side of the annular projection 117e, the cylindrical region 117b, and the inclined cylindrical region 113c correspond to the storage tube, and the cylindrical region 113b corresponds to the carrier accommodating tube. However. if a carrier is accommodated in the inclined cylindrical region 113c, the inclined cylindrical region 113c corresponds to the carrier accommodating tube.

Figure 11:
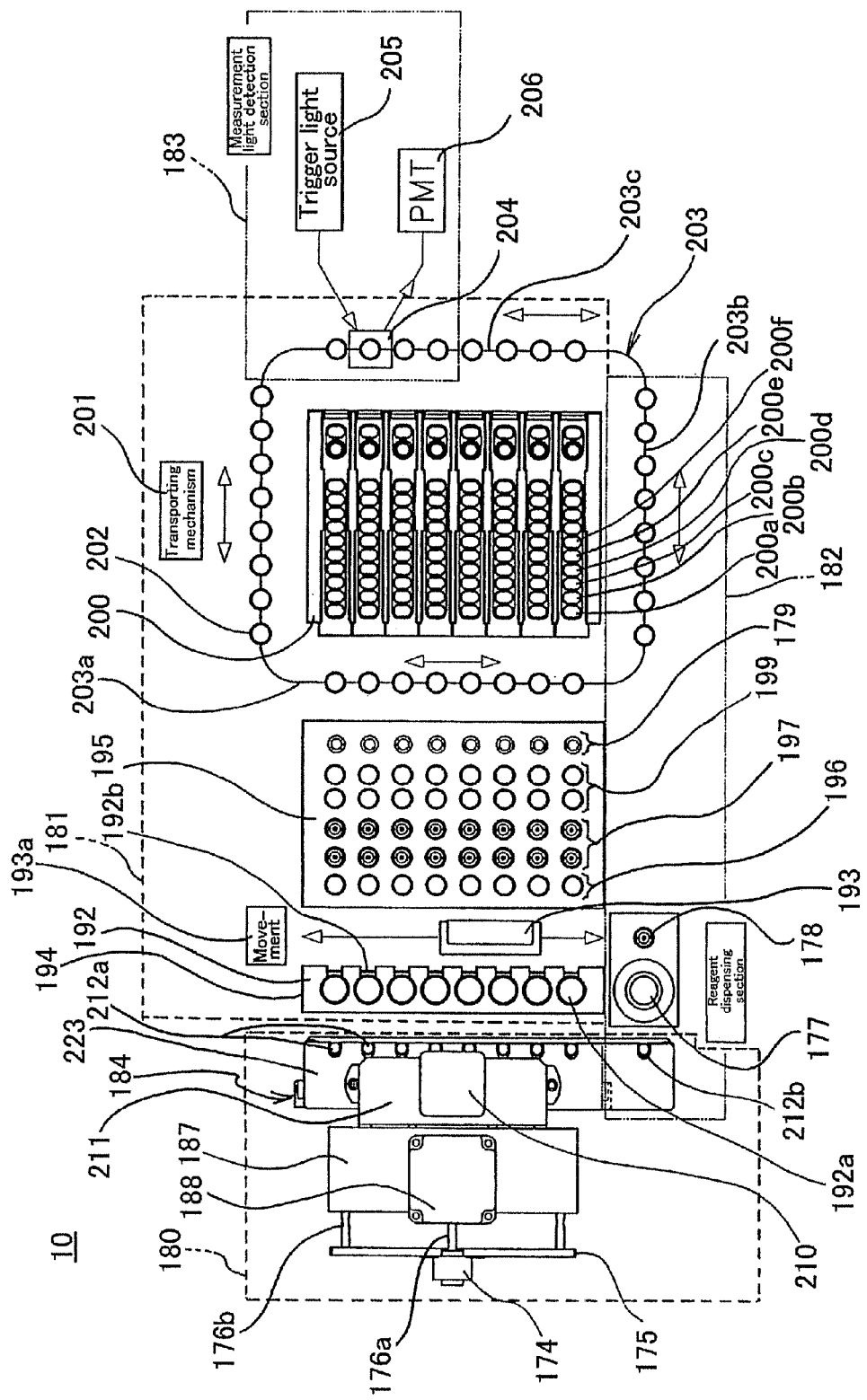
FIG. 11 shows a carrier treating apparatus according to an eleventh embodiment of the present invention.

Next, FIG. 11 is a schematic plan view showing an overall carrier treating apparatus 10 according to an eleventh embodiment of the present invention.

The carrier treating apparatus 10 comprises: a carrier enclosing tip treating apparatus 180 having a gas suction and discharge mechanism which, for example, fits the carrier enclosing tip 36 to a plurality of nozzles for performing suction and discharge treatment with respect to the tip 36; a carrier treatment region 181 where solutions containing various specimens and reagents are sucked or discharged into/ from the carrier enclosing tip 36, to thereby perform suction, discharge, dispensation into an external container, aggregation, washing, extraction, transfer, reaction, and the like of the previously prepared solutions with respect to the enclosed carrier; a reagent dispensation region 182 where a single individual nozzle of the carrier enclosing tip treating apparatus 180 is used to dispense a reagent mainly for measurement or the like required just before treatment, into the carrier enclosing tip 36; and a measurement region 183 where optical information is obtained to perform measurement on substances containing the carrier enclosed in the carrier enclosing tip 36.

Figure 12:
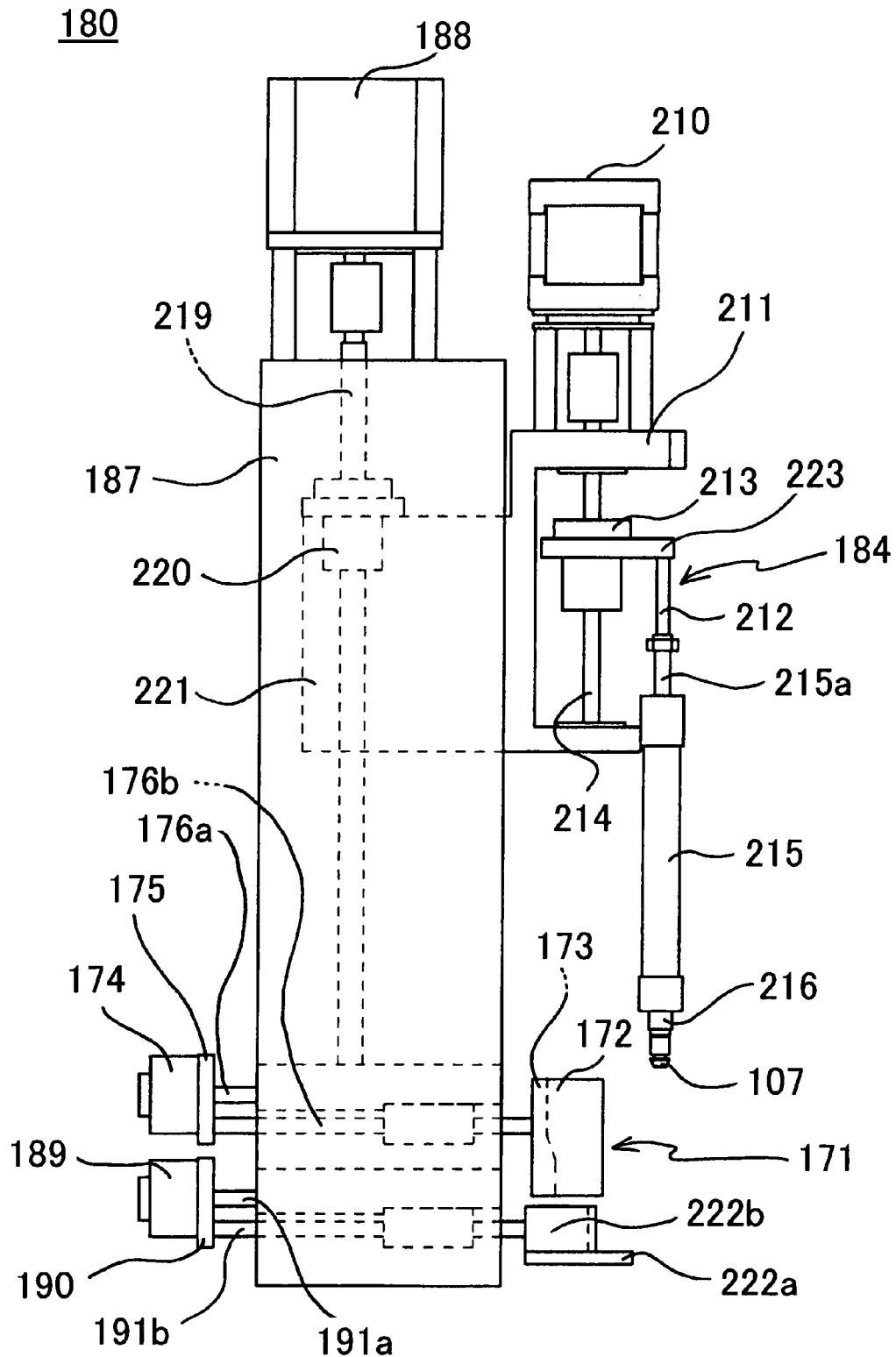
FIG. 12 shows a carrier enclosing tip treating apparatus according to the eleventh embodiment of the present invention.

The carrier enclosing tip treating apparatus 180 shown in FIG. 11 and FIG. 12 has a nozzle head 184 having a plurality (nine nozzles in this example) of nozzles 107 arranged in the row direction (longitudinal direction in the drawing), and gas suction and discharge are performed with respect to the nozzle head 184 at once. Of the nine nozzles 107, a nozzle 107 at one end is an individual nozzle, which is, as shown by its position (position of the reference symbol 212b in FIG. 11), provided slightly separate from the position of the eight nozzles 107, that is, the collective nozzles (position of the reference symbol 212a).

As shown in FIG. 12, the suction and discharge mechanism comprises: large diameter portions 216 provided on the slightly upper side of the respective nozzles 107; and rods 212 for sliding plungers 215a in cylinders 215 which are connected to the respective nozzles 107. Furthermore, the nine rods 212 are attached in such a manner that eight ends 212a and one end 212b radially projecting with a greater diameter than the diameter of the rod 212, are hooked on respective nine notches provided at the edge of a driving plate 223 which is vertically movable at once. The nozzle head 184 is moved in the line direction (transverse direction or left and right direction in the drawing [(FIG. 12)]).

Moreover, as shown in FIG. 12, the driving plate 223 is connected to nut 213 into which ball screw 214 is screwed. The respective rods 212 are always energized downward by a spring provided on the cylinder 215. Accordingly, the respective rods 212 are raised by the nut 213 when they are moved upward, whereas the respective rods 212 are lowered not by the nut 213 but by the spring force when they are moved downward. The ball screw 214 is rotatably driven by a motor 210 provided on a cross-sectional reverse C-shaped supporting member 221, and thereby the driving plate 223 and the nine rods 212 are vertically moved at once.

Of these nine nozzles 107, the individual nozzle is provided on the nozzle head 184, and thus suction and discharge is performed therein together with other eight collective nozzles at once. Moreover, the raising/lowering movement and the horizontal movement in the line direction (left and right direction in FIG. 11) are also performed at once. However, the individual nozzle is used for dispensing a reagent for measurement into the carrier enclosing tip 36, in the reagent dispensation region 182. When the individual nozzle is used, the carrier enclosing tip is removed from the other collective nozzles. Moreover, when the collective nozzles are used, the individual nozzle is not fitted with a tip or the like.

In FIG. 12, in a box case 187 are provided: a ball screw 219; a nut 220 into which a ball screw 219 is screwed; and a supporting body 221 which has the supporting member 211 attached the nut 220, on one end. Moreover, on the box case 187 is provided a motor 188 which rotatably drives the ball screw 219. The nozzles 107 are vertically movable at once by this rising/lowering mechanism constructed by these components.

On the lower side of the box case 187 is provided a temperature increasing/decreasing device 171. The temperature increasing/decreasing device 171 is formed along the row direction, so as to have a height and a width capable of coming close to or in contact with the nine tips fitted to the nine nozzles, and comprises: heating plates 173 having internal heaters; and ten sheets of heating walls 172 having internal heaters, which are attached to the heating plates 173, and are provided projectingly so as to sandwich the respective tips from the both sides. These heating plates 173 are preferably formed to have a shape matching with the shape of a tip serving as an object of temperature control. Here, the heating plates 173 and the heating walls 172 correspond to the temperature increasing/decreasing member.

The temperature increasing/decreasing device 171 comprises: a motor 174 for enabling approach to or contact with the tip fitted to the nozzles 107 of the nozzle head 184 to enable heating of the tips; a ball screw 176a which is rotatably driven by the motor 174; a nut 175 in which the ball screw 176a is screwed; and a moving rod 176b which is connected to the nut 175, is movable in the left and right direction of the drawing, and is also connected to the heating walls 172 and the heating plates 173.

On the lower side of the temperature increasing/decreasing device 171 are provided: a comb tooth-shaped catch 222*a*; nine magnets 222*b*; a motor 189 which moves in the left and right direction of the drawing, for enabling removal of the tips 36 fitted to the nozzles 107, or to apply a magnetic field; a moving support plate 190 which is movable in the left and right direction by the motor 189; and moving rods 191*a* and 191*b* attached to the moving support plate 190.

The carrier enclosing tip treating apparatus 180 is provided so as to be suspended from above, and is provided so as to be movable by an X axis (line direction) transfer mechanism utilizing a direct acting mechanism (not shown) so as to cover the overall area of the treating apparatus 10 and other necessary regions.

Moreover, returning to FIG. 11, the carrier treatment region 181 comprises: a cartridge container 192 having eight object substance accommodating wells 192*a* which accommodate a solution containing an object substance; a matrix-shaped container 195 having 5 row×8 line wells of well rows 196 and 197 and a well row 199 accommodating the product material; and eight cartridge containers 200 having wells 200*a* which can be prepacked for accommodating various reagents and substances for performing treatments, or resultant products. Of the cartridge containers 200, reference symbol 200*b* denotes incubating wells provided with heat blocks.

Furthermore, the object substance accommodating wells 192*a* are respectively attached with bar codes 192*b* showing information on the object substance. The bar codes 192*b* are read by a bar code reader 193 moving to scan the bar codes 192*b*. Reference symbol 193*a* denotes a transfer mechanism which drives the bar code reader 193.

To enclose the surroundings of the eight cartridge containers 200, there is provided a conveyer 203 which is movable along a rectangular conveyance path having: row conveyance paths 203*a* and 203*c* along row directions (longitudinal direction or Y direction in the drawing) that are parallel to the array direction of eight nozzles, on the movement path of the eight collective nozzles 107 of the carrier enclosing tip treating apparatus 180; and a line conveyance path 203*b* along a line direction (transverse direction or X direction) on the movement path of the individual nozzles 107 thereof. The conveyer 203 correspond to the line and row path conveyance device, and has a total of 32 tip accommodating sections or tubes 202 connected so as to match the clearance between the nozzles, in a manner so as to be movable together with the conveyer 203. Accordingly, in positions shown in FIG. 11, suction and discharge of liquid can be performed with respect to a group of two rows of tubes 202 arrayed on the row conveyance paths 203*a* and 203*c*, by eight nozzles of the carrier enclosing tip treating apparatus 180. Moreover, a reagent according to the purpose, such as a substrate solution for chemiluminescence can be dispensed into the selected tip accommodating sections or tubes 202 on the line conveyance path 203*b* on the lower side of the conveyance path arrayed in rectangular-shape as the line and row path conveyance device, that is, in the reagent dispensation region 182, by the individual nozzle 107 provided separately from the group of eight collective nozzles 107 in the treating apparatus 10.

Furthermore, a measurement point 204 is provided on the rectangular conveyance path of the line and row path conveyance device in the measurement region 183, so that the inside of the carrier enclosing tip is irradiated with exciting light at the measurement point 204 by the trigger light source 205 and generated light is received by the light receiver 206 to perform measurement. As a result, treatment can be performed according to the treatment purpose.

Although not shown in the figure, in order to control the carrier treating apparatus 10, an input unit for inputting instructions or data from users, a CPU which performs various processings such as calculation, a display device, various memories, and an information processor having a communication means and the like, instruct the suction and discharge mechanism of the carrier enclosing tip treating apparatus 180, the transfer mechanism, the line and row path conveyance device, and the devices in the measurement region 183, and/or receive signals from these devices. The information processor is provided with a controller which controls the amount, the speed, the number of times, the time, and the position of suction and discharge by the nozzle, according to material conditions including the structures of the nozzle, the member to be fitted to the nozzle, and the carrier enclosing tip, the type and concentration of the substance in the fluid, the amount of the fluid, the temperature of the fluid or the carrier, the coordinate position including the position of accommodation of the fluid, and the treatment contents.

Figure 13:
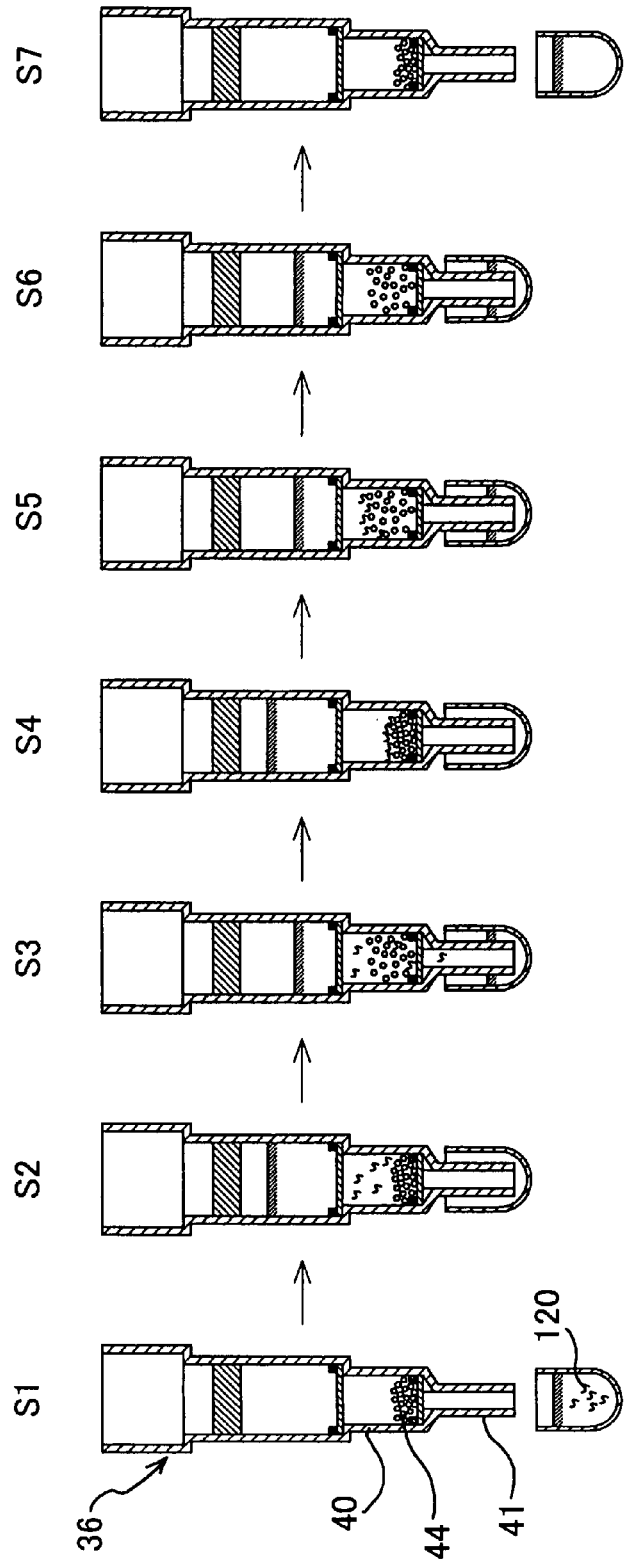
FIG. 13 shows a flowchart of carrier treatment according to a twelfth embodiment of the present invention.

Next is a description of treatment using the carrier enclosing tip 36 according to a twelfth embodiment of the present invention, with reference to FIG. 13. Here, separation and purification of mouse IgG (antibody) using a protein A are described as an example.

In Step S1, a particulate filler 44, specifically, an affinity ligand (such as an antibody, an antigen, a pigment, and an enzyme), here, a protein which exists in cell walls of *Staphylococcus aureus* and shows specificity to IgG derived from various animal hosts, is used as the carrier in the carrier enclosing tip 36. The protein A immobilized to a cross-linked agarose based chromatography gel, is used. The chromatography gel having the protein A immobilized to the surface thereof is enclosed, and the carrier enclosing tip 36 is fitted to the nozzle 107 of the nozzle head 184.

The carrier enclosing tip 36 is moved in the line direction together with the nozzle head 184, to a container containing a sample solution of culture supernatant containing a purification object 120 such as mouse IgG. In Step S2 to Step S4, the sample solution in the container is repeatedly sucked and discharged through the nozzle 107, to thereby mix and agitate the sample and the chromatography gel. In this case, since the protein A ligand has a small binding constant to IgG, the adsorbing ability is high even if the flow rate is as high as for example 1000 cm per hour. If the operation is performed with a dispensing tip, the operation can be performed at a linear flow rate of 300 cm to 500 cm per hour. By so doing, the mouse IgG serving as the purification object 120 is bound to or absorbed in the affinity ligand on the surface of the particulate filler 44 of the chromatography gel. These steps take about 5 minutes.

Next, in Step S5, the nozzle head 184 is moved to a container containing an appropriate solvent as a washing liquid. The carrier is washed by suction and discharge with the washing liquid. 20 mM sodium phosphate (pH 7.0) buffer solution which is also used as a sample diluent, is used as the washing liquid. The washing is repeated by changing the washing solution at least twice. By so doing, the culture supernatant which is the sample solution left in the tip is removed. Here, the amount of the buffer solution induced into the carrier enclosing tip 36 is controlled so as to be three times the volume of the carrier enclosed in the carrier enclosing tip 36. At this time, suction and discharge of the washing liquid may be repeated while the absorbance in the tip is monitored in the measurement region 183, until the absorbance comes below a certain value. In this case, as shown in FIG. 11, suction and discharge are performed while the tip 36 is mounted and conveyed on the conveyer 203 serving as the line and row path conveyance device, and measurement is repeated at the measurement point 204.

In Step S6, the carrier enclosing tip 36 is moved to a container containing a solvent which selectively elutes the object substance absorbed in the surface of the chromatography gel, from the gel, and then suction and discharge are repeated. As the eluent, for example, 0.1 M citric acid-NaOH (pH 3.0) is used. Besides this, glycine buffer or acetate buffer may be used. In this case, the pH is within a range between about 2.5 and 4. This step takes about 5 minutes.

In Step S7, the mouse IgG serving as the object substance is eluted in the solution, and discharged into a predetermined container. The elusion is observed as an absorbance peak (A280). Since this peak portion of IgG elusion is the target purified antibody (IgG), this peak portion is fractioned and collected while keeping an eye on the rising up at A280. After the elution operation is completed, an appropriate amount of 1M Tris-HCL (pH 8) is added so as to neutralize the pH of the IgG solution that has been eluted with the acidic buffer solution.

Furthermore, since the solution containing the eluted IgG still has eluent components and a high concentration of Tris, the solution has to be replaced with an appropriate buffer such as PBS by means of ultrafiltration. For this purpose, for example, the carrier enclosing tip 98 shown in FIG. 9 using an ultrafiltration membrane as the thin membranous carrier is prepared, and arranged in a tip accommodating row 179 of FIG. 11.

The carrier enclosing tip 36 is removed from the nozzle head 184, and a dispensing tip is newly fitted thereto. The solution containing the eluted IgG is sucked into the appropriate dispensing tip, and moved to, for example, the tip accommodating row 179 by the nozzle head 184. Then, the solution is discharged from the fitting opening 101 of the carrier enclosing tip 98, and is accommodated. Next, the dispensing tip is removed from the nozzle 107, and is fitted to the fitting opening 101 of the carrier enclosing tip 98 through the adaptor 108. Then, a treatment is performed in which the solution is pressurized using the suction and discharge mechanism to pass through the ultrafiltration membrane.

In the above treatment, the description is about the carrier enclosing tip 36 using a single nozzle. However, usage of a plurality of nozzles enables the performance of a plurality of treatments at once. Therefore, the treatment according to the present embodiment is more efficient than for conventional liquid chromatography or the like, since a large number of specimens can be handled at once with a small scale device.

Figure 14:
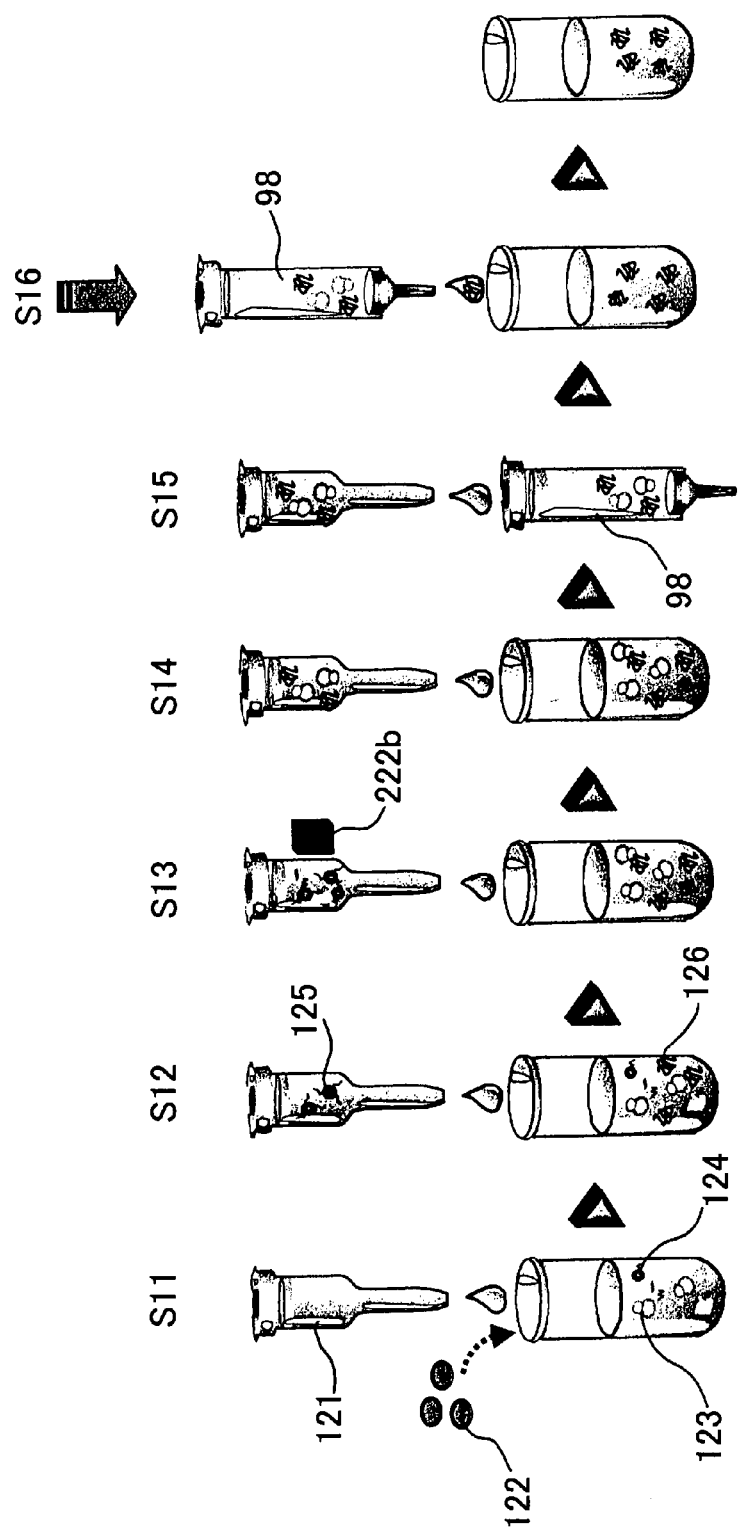
FIG. 14 shows a flowchart of carrier treatment according to a thirteenth embodiment of the present invention.

Next is a description of a treatment according to a thirteenth embodiment in which a target protein is synthesized and produced, with reference to FIG. 14. In Step S11, the reaction solution is produced by mixing. For this purpose, to the nozzle head 184 of the carrier enclosing tip treating apparatus 180 in the carrier treating apparatus 10 are attached eight dispensing tips 121, and then the nozzle head 184 is moved, to thereby suck and mix various reagents contained in wells of the eight cartridge containers 200, at a predetermined mixing ratio, that is, 2.5 microliters of positive control solution (DHFR) containing 0.5 μg of template DNA for synthesizing DNFR (dihydrofolic acid reductase) as the target protein, 25 microliters of Puresystem Sol.A (registered trademark), 10 microliters of Puresystem Sol.B (registered trademark), and 12.5 microliters of nuclease free water, and then dispense into the well 192 provided in the carrier treatment region 181 while controlling to make 50 microliters in total.

Here, the respective solutions of Puresystem contain protein factors required for transcription, translation, and energy regeneration, which are all separately prepared, produced, and reconstructed, namely; an initiation factor, an elongation factor, a termination factor, a ribosomal recycling factor, an aminoacyl-tRNA synthetase corresponding to 20 types of amino acids, and the like. Moreover, component proteins except for ribosome protein are all prepared in a state where the His-tag is added to N terminal or C terminal.

In this case, the treatment is performed in a state where the well 192 is cooled, for example, by being brought closer to ice. By so doing, as shown in FIG. 14, in the well 192 may be provided a reaction solution containing a template DNA 122, ribosome 123, a His-tagged factor, and the like. The reaction solution is sucked, and the nozzle head 184 is moved to the well 196 in a constant-temperature condition at 37° C. Then, the reaction solution is discharged and stored in the well 196, to effect a synthesis reaction of the target protein for one hour.

In Step S12, the reaction solution is sucked from the well 196, then the nozzle head 184 is moved, and again the solution is discharged into the well 192, which is then recooled by being brought closer to ice. In this state, 10 microliters of the suspension solution of the magnetic particles 125 is sucked from the well 200 storing magnetic particles 125 covered with a metal affinity resin, and then discharged into the well 192, and mixed and agitated therein. For this purpose, suction and discharge are repeated for about 10 minutes at a predetermined speed (such as several tens of microliters/sec).

In Step S13, while the well is cooled, the magnet 222b of the carrier enclosing tip treating apparatus 180 is brought closer to the dispensing tip 121 fitted to the nozzle head 184 from the outside of the dispensing tip 121, to apply a magnetic field. In this state, suction and discharge are performed at a predetermined speed (such as several tens of microliters/sec), so that the magnetic particles 125 are absorbed in the inner wall of the dispensing tip to separate (B/F separation).

Then, since the His-tag factor is bonded to the magnetic particles 125, removal of the magnetic particles enables removal of proteins other than the target synthetic protein.

In Step S14, 1.5 milliliters of the supernatant is sucked from the well 192 by the dispensing tip 121, and the nozzle head 184 is moved to the well row 199, where the supernatant is discharged. 50 microliters of nuclease free water is added into the well row 199 to make 100 microliters in total.

In Step S15, the solution is sucked into the dispensing tip 121, and discharged into the fitting opening 101 of the carrier enclosing tip 98 accommodated in the tip accommodating row 179. By so doing, the reaction solution is stored in the large diameter tube of the carrier enclosing tip 98. An ultrafiltration membrane is enclosed as the carrier of the carrier enclosing tip 98.

In Step S16, the dispensing tips 121 are hooked off from the respective nozzles 107 of the nozzle head 184 using the comb tooth-shaped catch 222a, then the respective nozzles 107 are inserted into the fitting openings 101 of the carrier enclosing tips 98 through the medium of the predetermined adaptors 108, so as to fit the carrier enclosing tip 98 to the nozzle 107. Next, while the carrier enclosing tip 98 is fitted, the nozzle head 184 is moved to the well row 199 on the top right in FIG. 11, and while the small diameter tube 103 of the carrier enclosing tip 98 is inserted in the well row 199, gas is discharged by the suction and discharge mechanism of the carrier enclosing tip treating apparatus 180, to thereby let the reaction solution contained in the large diameter tube 100 pass through the thin membranous filter 106 serving as the ultrafiltration membrane by pressurizing from the top. As a result, in the well row 199 can obtain the solution containing the target synthetic protein 126 from which ribosome is removed. According to the treatment according to the present embodiment, a large number of specimens can be spontaneously handled with a smaller scale of apparatus, compared to with conventional liquid chromatography or the like, and thus the efficiency is high.

The above procedure is merely exemplary. For example, the procedure of His-tag removal using the magnetic particles 125 in accordance with Step S12 and Step S13 may be performed after the procedure of ribosome removal from Step S14 to Step S16.

The abovementioned respective embodiments are specifically described for better understanding of the present invention, and not to be considered as limiting other embodiments. Therefore, modifications may be made without departing from the gist of the invention. For example, in the above embodiments, only the case of proteins was mainly described, however DNA substances, RNA, sugar chains, or the like may also be used. Moreover, as to the particulate carrier, only the case of a globular-shaped particulate carrier was described, however the present invention is not limited to this case, and the shape may be column-shape or rectangular-shape. Furthermore, the present invention may be applied to carriers of indeterminate form. Moreover, the numerical values, the number of times, the shape, the number, the volume, and the like are also not limited to these cases.

The above respective components, carrier enclosing tip, carrier, tip-like container, enclosing section, nozzle, heating device, and other devices, may be optionally combined with appropriate modification. Furthermore, the ligand is not limited to DNA, but includes genetic materials such as oligonucleotide and RNA, immunity substances, proteins, sugar chains, pheromones, allomones, mitochondria, virus, plasmids, and the like.

The abovementioned reagents and substances are merely exemplary, and other reagents and substances may be used. Moreover, the carrier capturing DNA or the like may be taken out from the narrow tube, and may be used as the object of preservation or other treatments. Furthermore, cases where the projections, the slopes, and the steps are provided in 1, 2, or 3 points in the tip-like container, are described, however the present invention is not limited to these cases and they may be provided in 4 points or more.

INDUSTRIAL APPLICABILITY

The present invention relates to a carrier enclosing tip, a carrier treating apparatus, and a method of carrier treatment. The present invention relates to various fields which require handling of biopolymer or biological low molecular materials such as genes, immune systems, amino acids, proteins, sugars, for example, industrial fields, agricultural fields such as food, agricultural production, and fishery processing, pharmaceutical fields, medical fields such as sanitation, health, immunization, diseases, genetics, scientific fields such as chemistry and biology, and the like. The present invention is an effective method particularly for continuously performing a series of treatments using a large number of reagents and substances in a predetermined order.

BRIEF DESCRIPTION OF THE REFERENCE SYMBOLS

10. Carrier treating apparatus
11, 25, 36, 51, 63, 71, 83, 86, 98, 111. Carrier enclosing tip
18, 32, 44, 58. Particulate filler (carrier)
69. Block-shaped filler (carrier)
82, 95. Block-shaped filter (carrier)
84, 106, 118 Thin membranous filter (carrier)

The invention claimed is:

1. A carrier treating apparatus comprising:
    a nozzle head having a first nozzle which performs gas suction and discharge;
    a suction and discharge mechanism which performs gas suction and discharge through the first nozzle;
    a carrier enclosing tip which is fitted or fittable to said first nozzle or a member to be fitted to the first nozzle;
    a carrier enclosed in the carrier enclosing tip, wherein the carrier is capable of adsorbing or capturing a biosubstance in a fluid, or capable of reacting with or binding to the biosubstance;
    a stage provided with a group of liquid accommodating sections which accommodate or are capable of accommodating various liquids;
    a moving device which moves said nozzle head relatively to said group of liquid accommodating sections;
    a temperature increasing/decreasing member which increases/decreases the temperature of the fluid by external signals, and which is provided close to, or so as to be capable of coming close to, the outside of said carrier enclosing tip so that the temperature of the fluid can be controlled while the carrier is enclosed in the carrier enclosing tip; and
    a controller which controls the gas suction and discharge through the first nozzle, according to items selected from the structures of the first nozzle, the member to be fitted to the nozzle, and the carrier enclosing tip; the type and concentration of the substance in the fluid, the amount of the fluid, the temperature of the fluid or the carrier, the coordinate position including the position of accommodation of the fluid, and the treatment contents, and the controller controls the fluid based on the treatment contents,
    wherein said carrier enclosing tip comprises:
        a tip-like container having a fitting opening which is fittable to the first nozzle for use in gas suction and discharge, or to the member to be fitted to the first nozzle, and
        a port through which inflow and outflow of the fluid can be effected by said gas suction and discharge,
    and wherein said tip-like container is provided with an enclosing section which encloses said carrier in said tip-like container so that said carrier can be in contact with the fluid that has flowed into said tip-like container.

2. The carrier treating apparatus according to claim 1, wherein the portion of the carrier enclosing tip enclosing the carrier has a volume in a range of 2 microliters to hundreds of microliters.

3. The carrier treating apparatus according to claim 1, wherein: said nozzle head has a single individual nozzle and a plurality of collective nozzles arranged in the row direction, both of which are arranged in the row direction; the first nozzle is one of the collective nozzles in the plurality of collective nozzles; said suction and discharge mechanism performs gas suction and discharge with respect to the single individual nozzle and the plurality of collective nozzles of the nozzle head at once; and said moving device comprises a nozzle head moving device which moves the nozzle head relatively to said group of accommodating sections along said line direction, and a line and row path conveyance device which has a conveyance path including a row conveyance path on the movement path of said collective nozzles along said row direction and a line conveyance path on the movement path of said single individual nozzle along said line direction, and conveys tip-like containers detached from said collective nozzles or a conveyance accommodating section capable of accommodating each liquid discharged from said collective nozzle head, along said conveyance path.

4. The carrier treating apparatus according to claim 3, wherein a light receiving device which receives light inside the detached tip-like container, is provided in a predetermined position along said conveyance path of said line and row path conveyance device.

* * * * *